US012226517B2

(12) United States Patent
Galanin

(10) Patent No.: US 12,226,517 B2
(45) Date of Patent: Feb. 18, 2025

(54) TOPICAL COMPOSITIONS AND METHODS TO PROMOTE OPTIMAL DERMAL WHITE ADIPOSE TISSUE COMPOSITION IN VIVO

(71) Applicant: Ivan Galanin, New York, NY (US)

(72) Inventor: Ivan Galanin, New York, NY (US)

( * ) Notice: Subject to any disclaimer, the term of this patent is extended or adjusted under 35 U.S.C. 154(b) by 210 days.

(21) Appl. No.: 17/288,728

(22) PCT Filed: Oct. 24, 2019

(86) PCT No.: PCT/US2019/057822
§ 371 (c)(1),
(2) Date: Apr. 26, 2021

(87) PCT Pub. No.: WO2020/086820
PCT Pub. Date: Apr. 30, 2020

(65) Prior Publication Data
US 2021/0401728 A1 Dec. 30, 2021

Related U.S. Application Data

(60) Provisional application No. 62/751,222, filed on Oct. 26, 2018.

(51) Int. Cl.
A61K 36/00 (2006.01)
A61K 8/92 (2006.01)
A61K 8/9794 (2017.01)
A61Q 19/08 (2006.01)

(52) U.S. Cl.
CPC ............ *A61K 8/922* (2013.01); *A61K 8/9794* (2017.08); *A61Q 19/08* (2013.01); *A61K 2800/10* (2013.01); *A61K 2800/74* (2013.01)

(58) Field of Classification Search
CPC .................................................. A61K 2800/10
See application file for complete search history.

(56) References Cited

U.S. PATENT DOCUMENTS

| | | | |
|---|---|---|---|
| 5,384,123 A | 1/1995 | Metsada | |
| 5,705,170 A | 1/1998 | Kong et al. | |
| 5,939,082 A | 8/1999 | Oblong et al. | |
| 6,361,806 B1 * | 3/2002 | Allen ................. | A61K 31/201 514/886 |
| 8,242,171 B2 | 8/2012 | Sinclair et al. | |
| 8,529,925 B2 | 9/2013 | Alexiades-Armenakas | |
| 2002/0106388 A1 | 8/2002 | Pugliese | |
| 2003/0198657 A1 | 10/2003 | Menon et al. | |
| 2009/0253666 A1 | 10/2009 | Lintner et al. | |
| 2013/0195925 A1* | 8/2013 | Arshed ................ | A23P 10/30 424/62 |
| 2013/0224318 A1 | 8/2013 | Hwang et al. | |
| 2013/0324468 A1 | 12/2013 | Cipolla | |
| 2014/0148504 A1 | 5/2014 | Hwang et al. | |
| 2014/0348961 A1 | 11/2014 | Shimada et al. | |
| 2016/0324817 A1 | 11/2016 | Aho et al. | |
| 2017/0071902 A1 | 3/2017 | Takemoto et al. | |

FOREIGN PATENT DOCUMENTS

| | | | | |
|---|---|---|---|---|
| CN | 107308438 A | * | 11/2017 | |
| FR | 2 845 912 A1 | | 4/2004 | |
| JP | 2009-51790 A | | 3/2009 | |
| JP | 2009-545582 A | | 12/2009 | |
| JP | 2012-512215 | | 5/2012 | |
| JP | 2013-224326 A | | 10/2013 | |
| JP | 2013-237629 A | | 11/2013 | |
| JP | 2015-511585 A | | 4/2015 | |
| JP | 2017-502972 A | | 1/2017 | |
| KR | 10-1406110 B1 | | 7/2014 | |
| WO | WO-0197777 A1 | * | 12/2001 | ............ A61K 47/14 |
| WO | WO 2004/003179 A1 | | 1/2004 | |
| WO | WO 2012/130775 A1 | | 10/2012 | |
| WO | WO 2015/123115 A1 | | 8/2015 | |

OTHER PUBLICATIONS

Akhtar et al., Physicochemical study of deodorization distillate of cotton seed oil. Journal of Natural Sciences and Mathematics (1982), 22(2), 89-102 (Year: 1982).*
Tuntiyasawasdikul et al, A monolithic drug-in-adhesive patch of methoxyflavones from Kaempferia parviflora : In vitro and in vivo evaluation. International Journal of Pharmaceutics (Amsterdam, Netherlands) (2015), 478(2), 486-495 (Year: 2015).*
Khaetthareeya, Solid lipid nanoparticles for topical administration of Kaempferia parviflora extracts. Journal of biomedical nanotechnology, (Apr. 2009) vol. 5, No. 2, pp. 224-232 (Year: 2009).*
Chinese-language Office Action issued in Chinese Application No. 201980069178.2 dated Jan. 10, 2023 with English translation (17 pages).
International Search Report (PCT/ISA/210) issued in PCT Application No. PCT/US2019/057822 dated Jan. 9, 2020 (three (3) pages).
Written Opinion (PCT/ISA/237) issued in PCT Application No. PCT/US2019/057822 dated Jan. 9, 2020 (nine (9) pages).
Extended European Search Report issued in European Application No. 19877355.8 dated Nov. 28, 2022 (15 pages).
"Night Cleansing Cream", MINTEL, Jun. 23, 2017, pp. 1-6, XP055982743, (six (6) pages).
Chinese-language Office Action issued in Chinese Application No. 201980069178.2 dated Oct. 26, 2023 with English translation (8 pages).
Japanese-language Office Action issued in Japanese Application No. 2021-547655 dated Nov. 24, 2023 with English translation (4 pages).
Declaration of Amit Matta (ten (10) pages), 2024.
Email from Walter Scott dated Mar. 15, 2024 (two (2) pages).
Chinese-language Office Action issued in Chinese Application No. 201980069178.2 dated Mar. 27, 2024 with English translation (8 pages).
European Office Action issued in European Application No. 19 877 355.8 dated Jun. 4, 2024 (12 pages).

(Continued)

*Primary Examiner* — Qiuwen Mi
(74) *Attorney, Agent, or Firm* — Crowell & Moring LLP

(57) ABSTRACT

Topical compositions and methods are provided that are effective for promoting an optimal composition of dermal white adipose tissue in vivo comprising an adipogenic agent, a retarder of lipogenesis or lipolytic agent and at least one penetrant.

2 Claims, 19 Drawing Sheets

(56) References Cited

OTHER PUBLICATIONS

Third Party Observation issued in European Application No. 19877355.8 dated Apr. 5, 2024 (8 pages).
Third Party Observation issued in European Application No. 19877355.8 dated Apr. 5, 2024 (6 pages).
Jang, H. et al., "Safety Evaluation of Polyethylene Glycol (PEG) Compounds for Cosmetic Use", Toxicological Research Official Journal of Korean Society of Toxicology, Jun. 2015, pp. 105-136, vol. 31, No. 2 (32 pages).
Apelblat, A. et al., "Extraction of Oleic Acid from Soybean Oil and Jojoba Oil-Phase Diagrams", JAOCS, Feb. 1996, pp. 239-244, vol. 73, No. 2 (6 pages).
Kassem, A. et al., "Influence of some humectants on the physical characteristics of solidified sodium stearate-based sticks", International Journal of Cosmetic Science, Feb. 1984, pp. 13-31, vol. 6 (19 pages).
Wattanasri, P. et al., "Development of *Kaempferia parviflora* extract-loaded microemulsions for skin permeation enhancement", Thai Journal of Pharmaceutical Sciences, 2016, pp. 37-40, vol. 40, Supplement Issue (4 pages).
Burnett, C. et al., "Safety Assessment of Plant-Derived Fatty Acid Oils", International Journal of Toxicology, Nov. 2017, pp. 51S-129S, vol. 36, Supplement 3 (79 pages).
Dąbrowski, G. et al., "Variation in oil quality and content of low molecular lipophilic compounds in chia seed oils", International Journal of Food Properties, Aug. 30, 2018, pp. 2016-2029, vol. 21, No. 1 (15 pages).
Anwar, A. et al., "Analytical Characterization of Hemp (*Cannabis sativa*) Seed Oil from Different Agro-ecological Zones of Pakistan", JAOCS, Apr. 2006, pp. 323-329, vol. 83, No. 4 (7 pages).
"Look forthese superstar ingredients in your skin care products", AMG Blog, Feb. 22, 2018 (4 pages).
Naik, A et al., "Mechanism of oleic acid-induced skin penetration enhancement in vivo in humans", Journal of Controlled Release, Dec. 1995, pp. 299-306, vol. 37 (8 pages).
Williams, A. et al., "Penetration enhancers", Advanced Drug Delivery Reviews, Dec. 2012, pp. 128-137, vol. 64 (10 pages).
Atef, E. et al., "Using Raman Spectroscopy in Studying the Effect of Propylene Glycol, Oleic Acid, and Their Combination on the Rate Skin", AAPS PharmSciTech, Jun. 15, 2017, pp. 114-122, vol. 19, No. 1 (9 pages).
Communication pursuant to Rule 114(2) EPC issued in European Application No. 19877355.8 dated Oct. 7, 2024 (19 pages).
Uto-Kondo, H. et al., "Tocotriencol Suppresses Adipocyte Differentiation and Akt Phosphorylation in 3T3-L1 Preadipocytes[1-3]", The Journal of Nutrition, Nutrient Physiology, Metabolism, and Nutrient-Nutrient Interactions, American Society for Nutrition, 2009, pp. 51-57, vol. 139, (7 pages).
Pang, K. et al., "The Role of Tocotrienol in Protecting Against Metabolic Diseases", Molecules, 2019, pp. 1-25, vol. 24, No. 923 (25 pages).
Katkade, MB et al., "Fatty acid profile and quality assessment of safflower (*Carthamus tinctorius*) oil", Journal of Pharmacognosy and Phytochemistry, 2018, vol. 7, No. 2, pp. 3581-3585, vol. 7, No. 2 (5 pages).

Hou, N. et al., "Quality and active constituents of safflower seed oil: A comparison of cold pressing, hot pressing, Soxhlet extraction and subcritical fluid extraction", Food Science and Technology, 2004, pp. 1-10, vol. 200, Elsevier Ltd. (10 pages).
Su, T. et al., "Apigenin inhibits STAT3/CD36 signaling axis and reduces visceral obesity", Pharmacological Research, 2020, pp. 1-11, vol. 152, Elsevier Ltd. (13 pages).
Torres-Villarreal, D. et al., "Anti-obesity effects of kaempferol by inhibiting adipogenesis and increasing lipolysis in 3T3-L1 cells", Journal of Physiology and Biochemistry, 2019, pp. 83-88, vol. 75, Springer (6 pages).
Yang, X. et al., "Green tea extracts reduce adipogenesis by decreasing expresson of transcription factors C/EBPα and PPARγ expression", Int J Clin Exp Med, 2014, pp. 4906-4914, vol. 7, No. 12 (9 pages).
Lee, O. et al., "Pycnogenol® Inhibits Lipid Accumulation in 3T3-L1 Adipocytes with the Modulation of Reactive Oxygen Species (ROS) Production Associated with Antioxidant Enzyme Responses", Phytotherapy Research, 2012, pp. 403-411, vol. 26, John Wiley & Sons, Ltd. (9 pages).
Jack, B., "An investigation into the Anti-obesity properties of *Cyclopia*", Dec. 2016, pp. i-xxiv and 1-231, Stellenbosch University (255 pages).
Shi, Z. et al., "Natural Extracts from White Common Bean (*Phaseolus vulgaris* L.) Inhibits 3T3-L1 Adipocytes Differentiation", Applied Sciences, 2021, pp. 1-11, vol. 11, No. 167 (11 pages).
Park, J. et al., "The protective effect of *Kaempferia parviflora* extract on UVB-induced skin photoaging in hairless mice", Photodermatology, Photoimmunology & Photomedicine, 2014, pp. 237-245, vol. 30, John Wiley & Sons Ltd (9 pages).
Kim, J. et al., "5,7-Dimethoxyflavone, an acitivator of PPARα/γ, inhibits UVB-induced MMP expression in human skin fibroblast cells", Experimental Dermatology, 2012, pp. 211-216, vol. 21, John Wiley & Sons Ltd (6 pages).
Ergönül, P. et al., "Identification of bioactive compounds and total phenol contents of cold pressed oils from safflower and camelina seeds", Journal of Food Measurement and Characterization, 2018 pp. 2313-2323, vol. 12, Springer (11 pages).
Guo, X. et al., "Synergistic interactions of apigenin, naringin, quercetin and emodin on inhibition of 3T3-L1 preadipocyte differentiation and pancreas lipase activity", Obesity Research & Clinical Practice, 2016, pp. 327-339, vol. 10, Elsevier Ltd (13 pages).
Lee, Y. et al., "Kaempferol suppreses lipid accumulation by inhibiting early adipogenesis in 3T3-L1 cells and zebrafish", Food & Function, 2015, pp. 2824-2833, vol. 6, The Royal Society of Chemistry (10 pages).
Korean-language Office Action issued in Korean Application No. 10-2021-7015458 dated Oct. 16, 2024 with English translation (13 pages).
Examination Report pursuant to Article 94(3) EPC, twelve (12) pages, dated Dec. 13, 2024.
Product of Lavoiser Health—"Advanced Breast Therapy"—Dec. 2015, eight (8) pages.

* cited by examiner

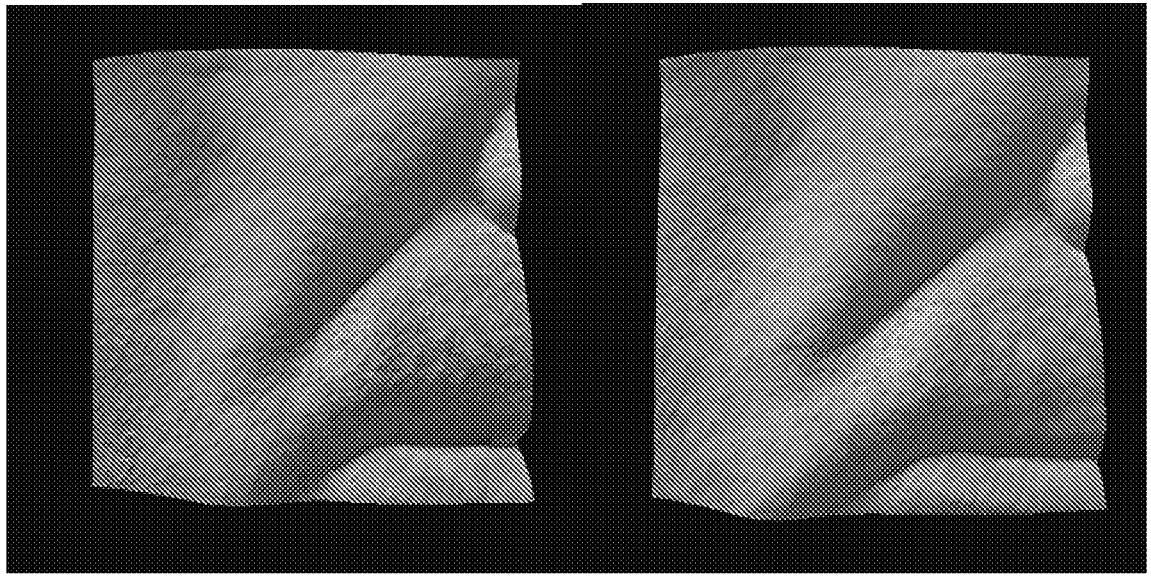
FIG. 2A   FIG. 2B
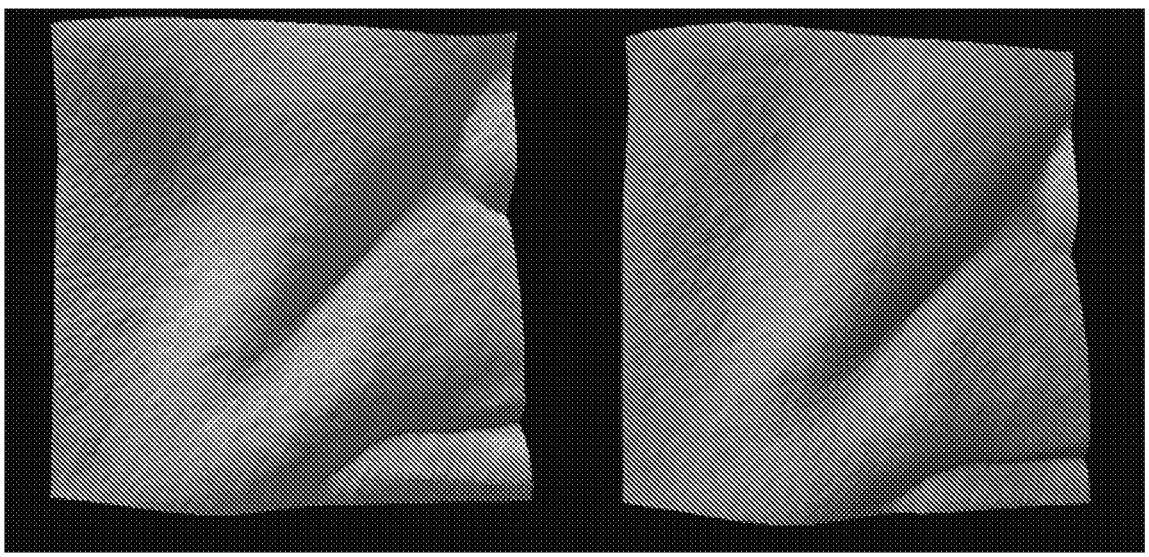
FIG. 2C   FIG. 2D

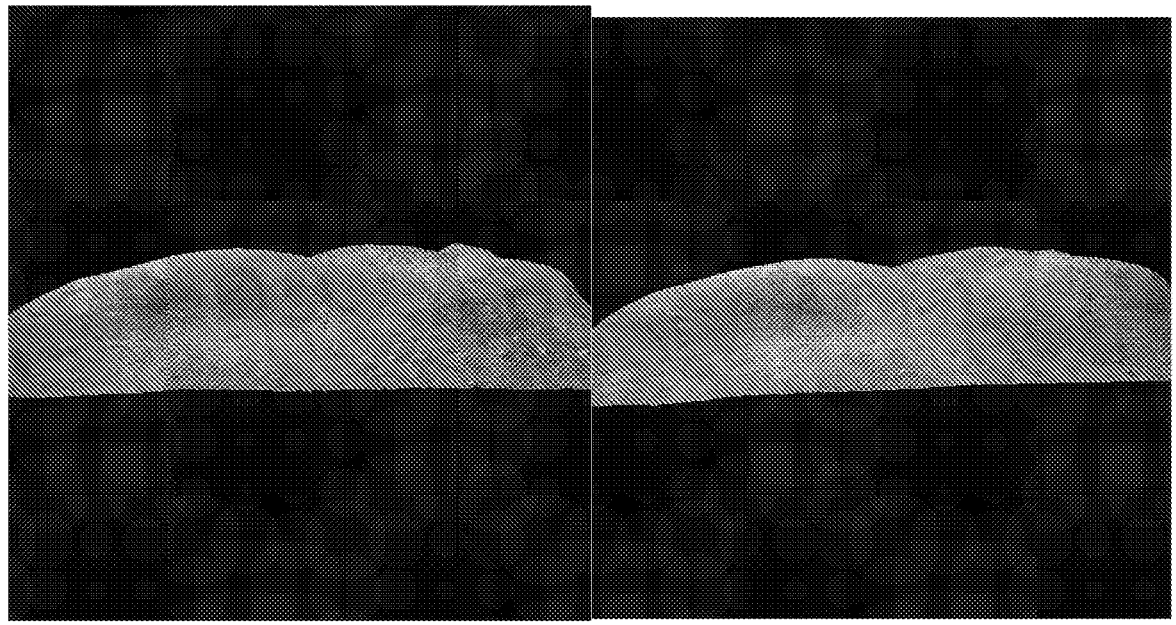
FIG. 3A  FIG. 3B
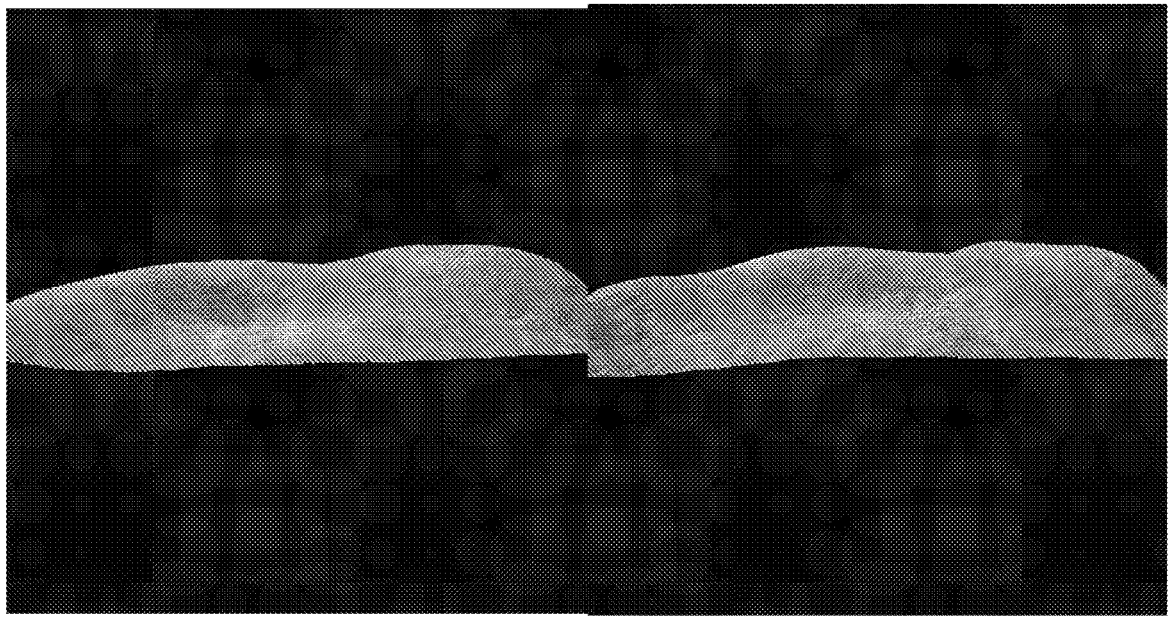
FIG. 3C  FIG. 3D

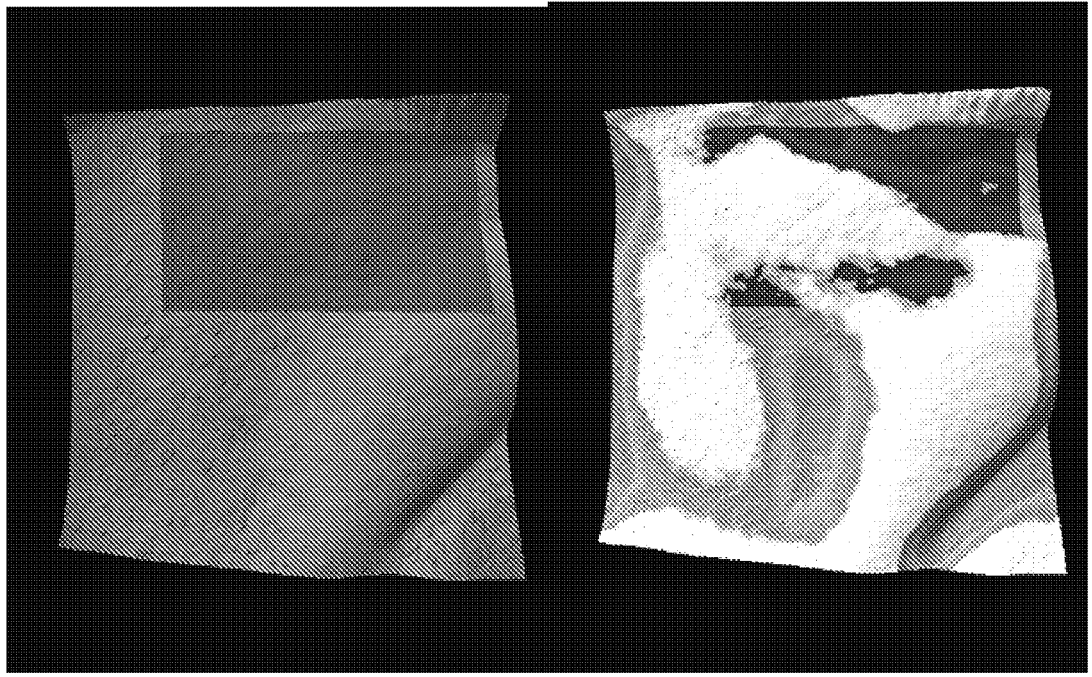
FIG. 4A  FIG. 4B
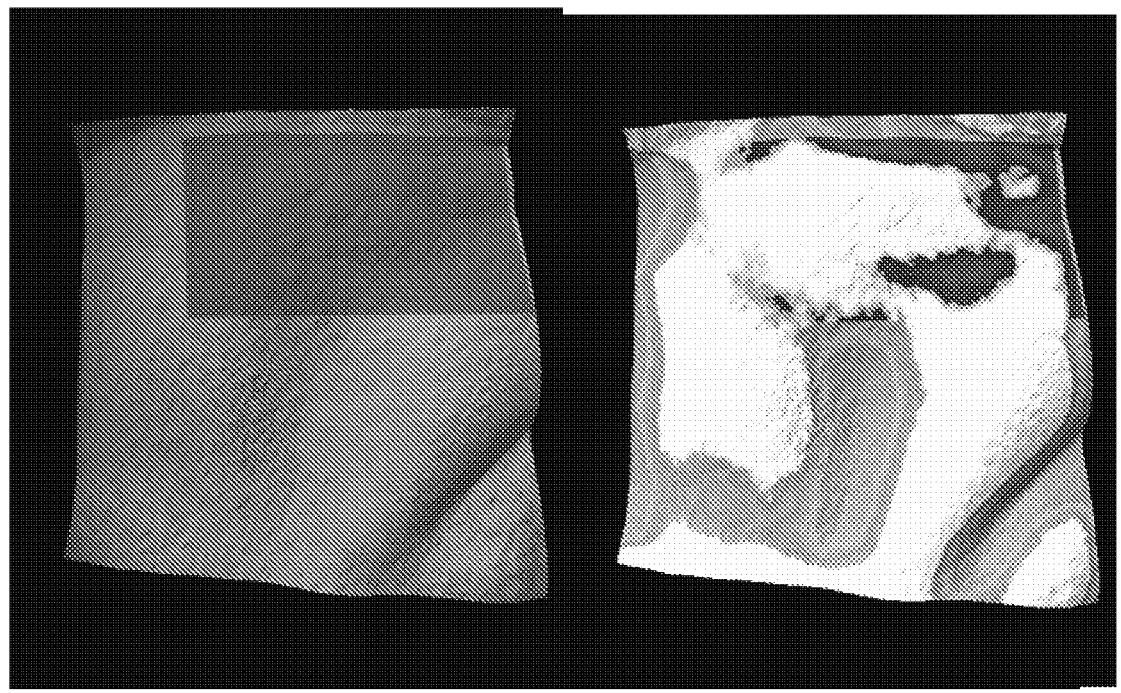
FIG. 4C  FIG. 4D

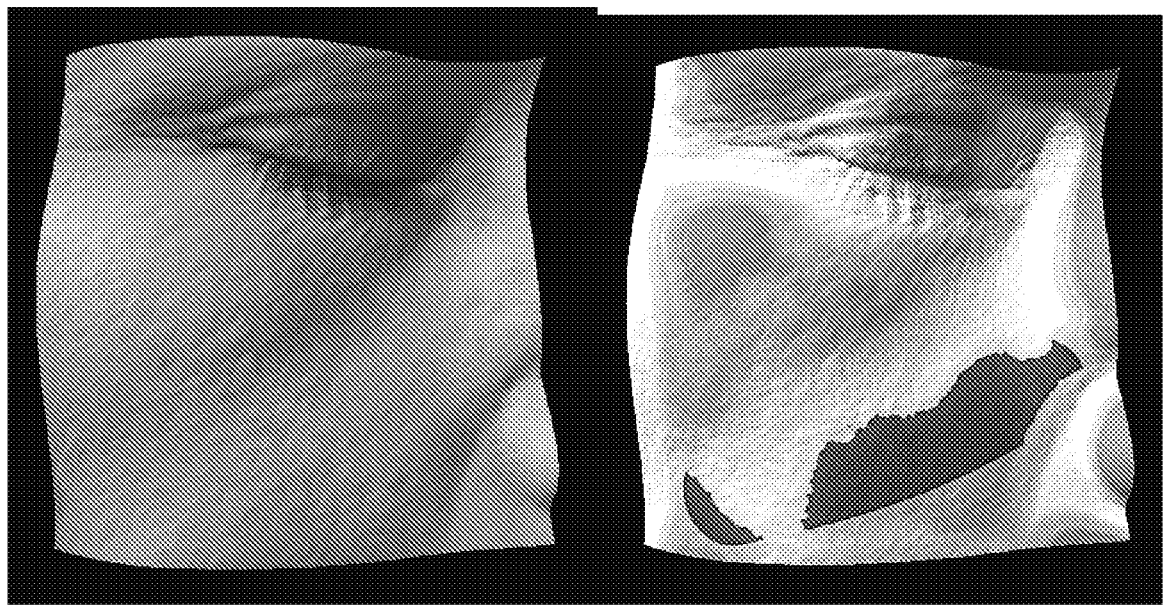
FIG. 6D  FIG. 6E
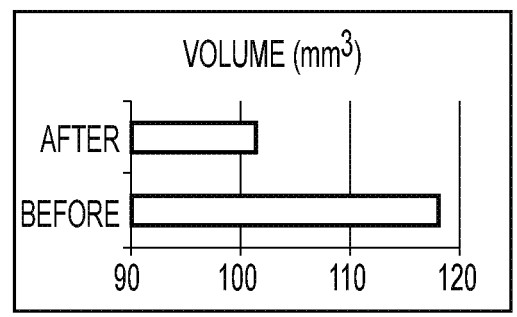
FIG. 6G
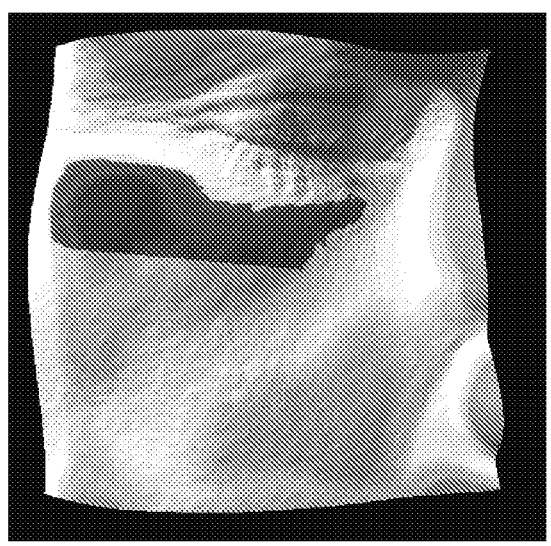
FIG. 6F
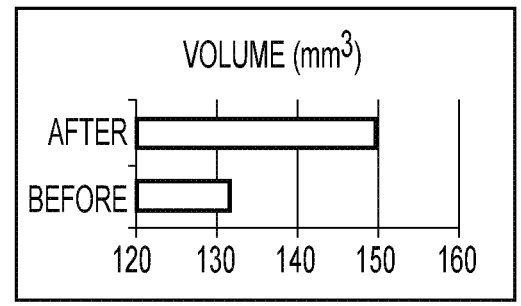
FIG. 6H

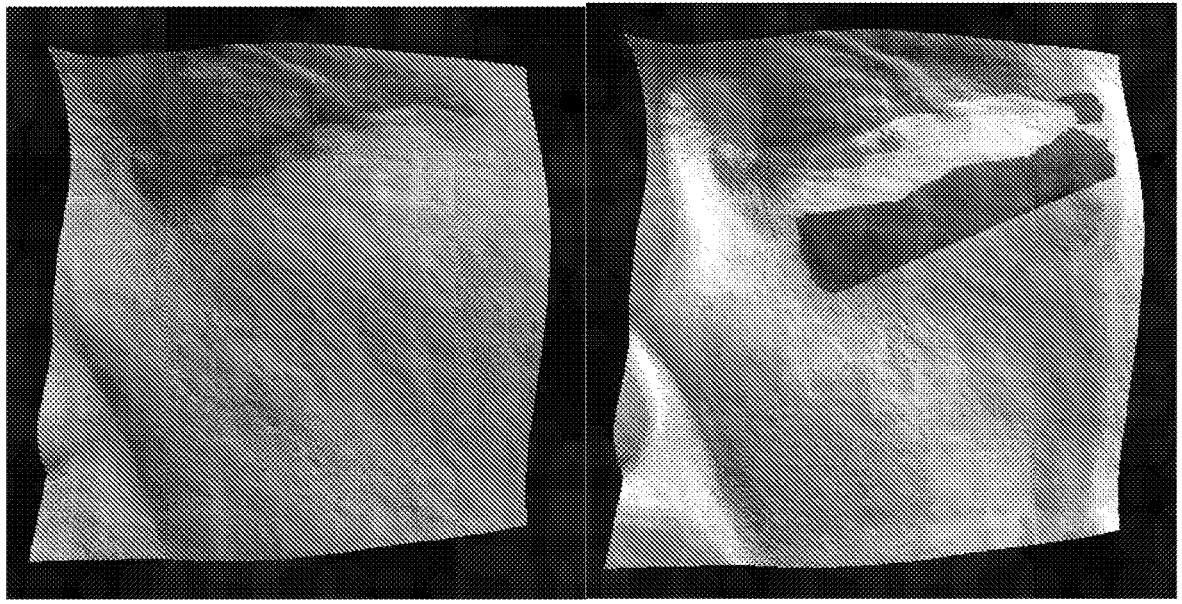
FIG. 7A  FIG. 7B
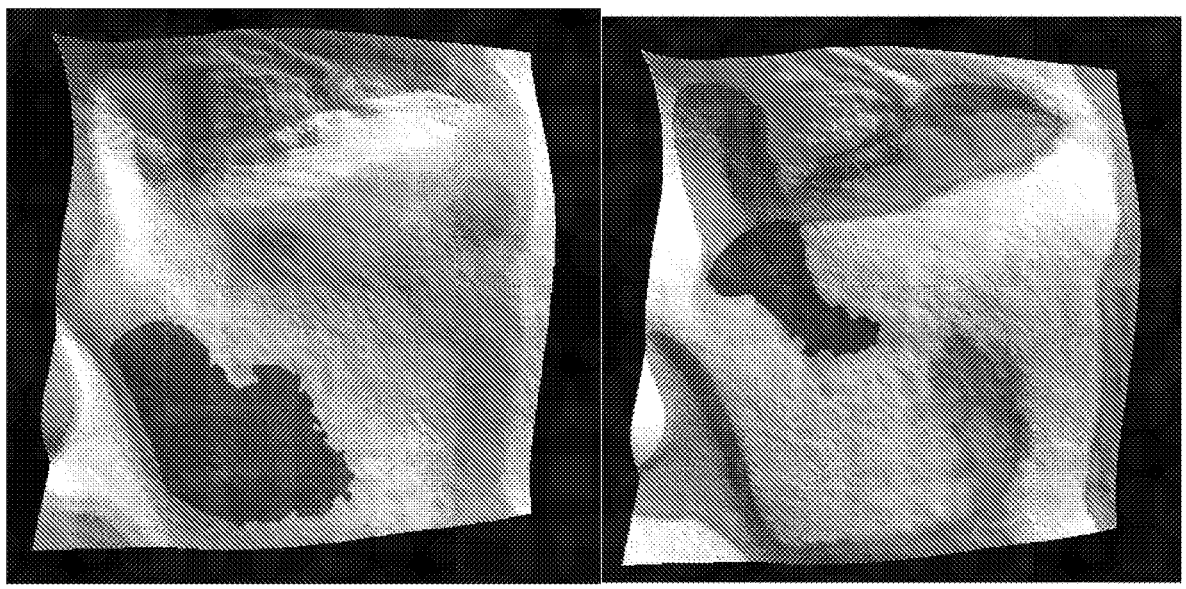
FIG. 7C  FIG. 7D

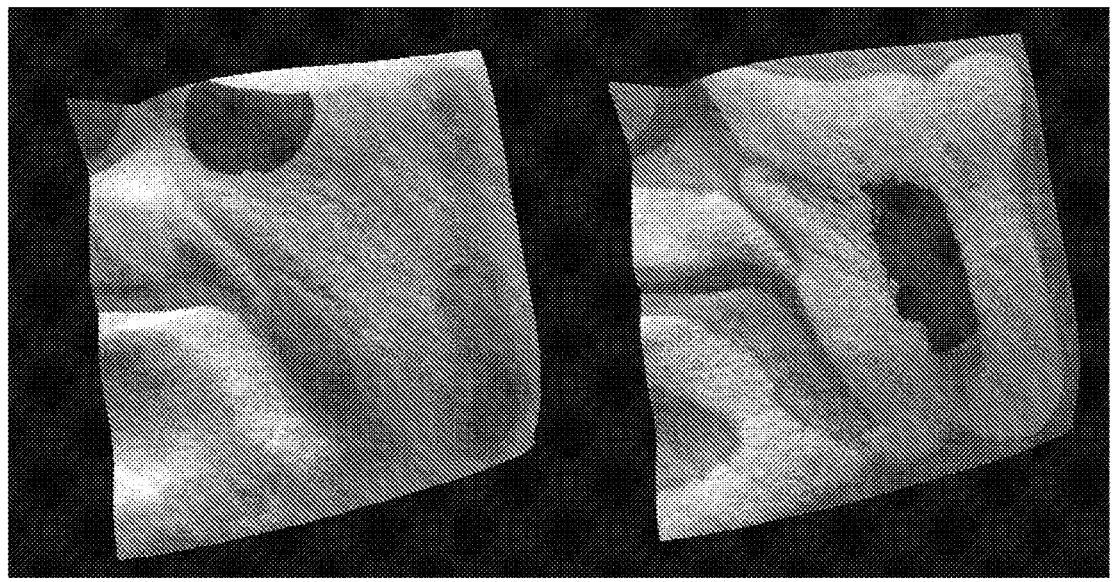
FIG. 8E    FIG. 8F
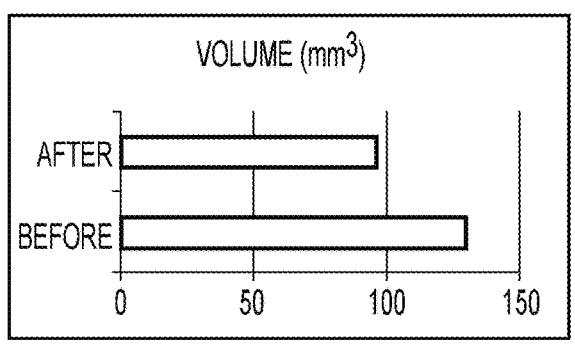    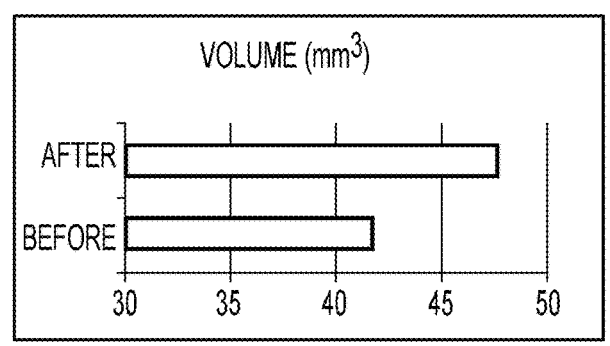
FIG. 8G    FIG. 8H

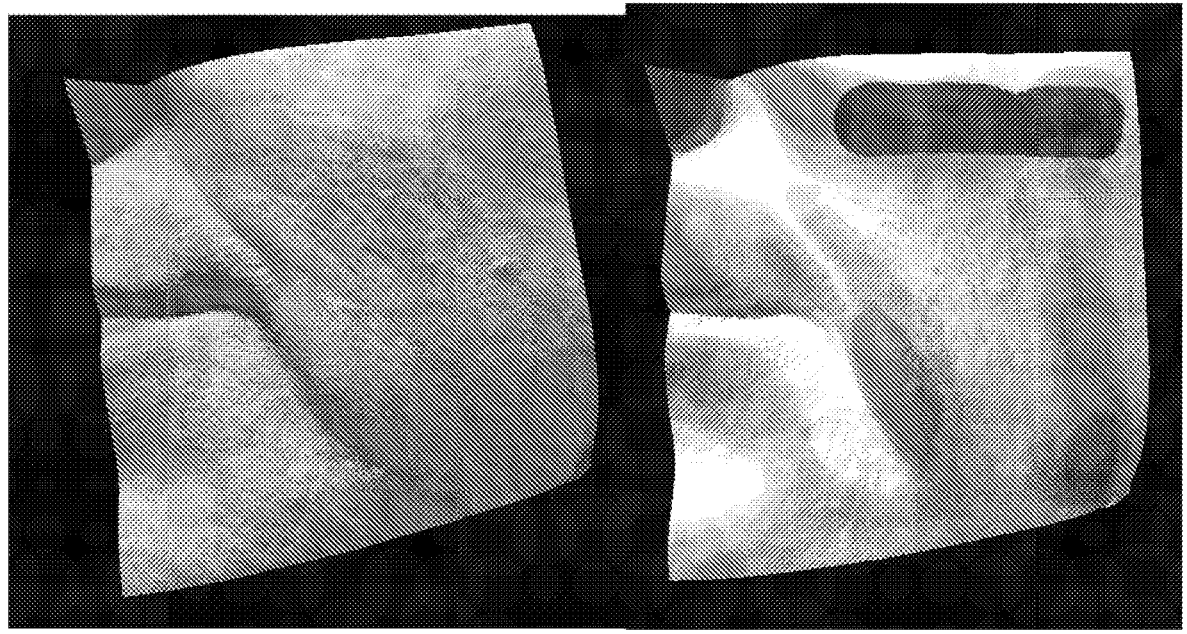
FIG. 9A  FIG. 9B
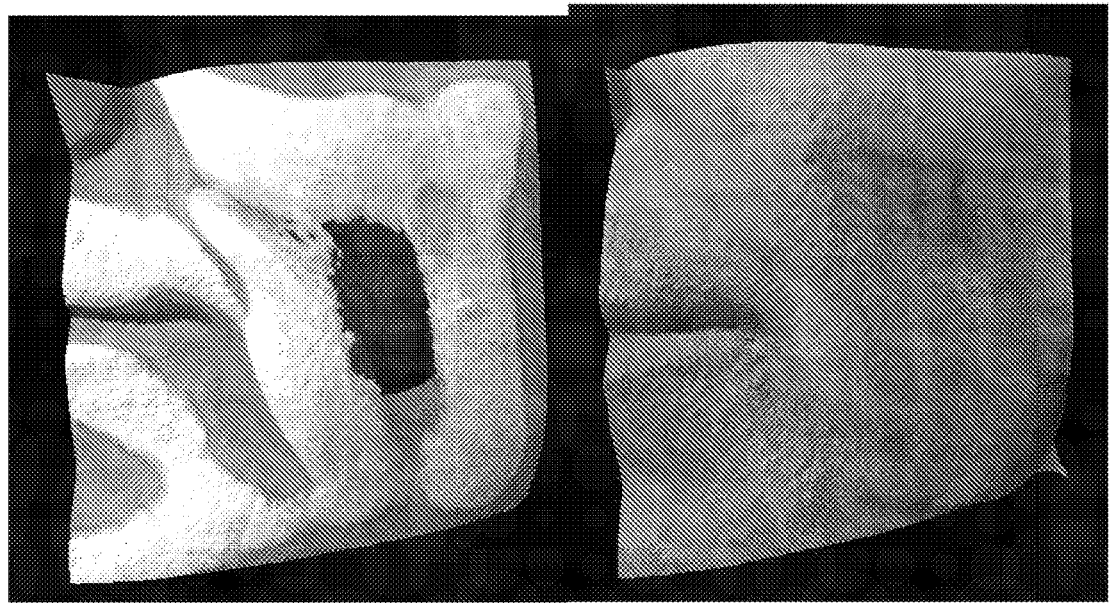
FIG. 9C  FIG. 9D

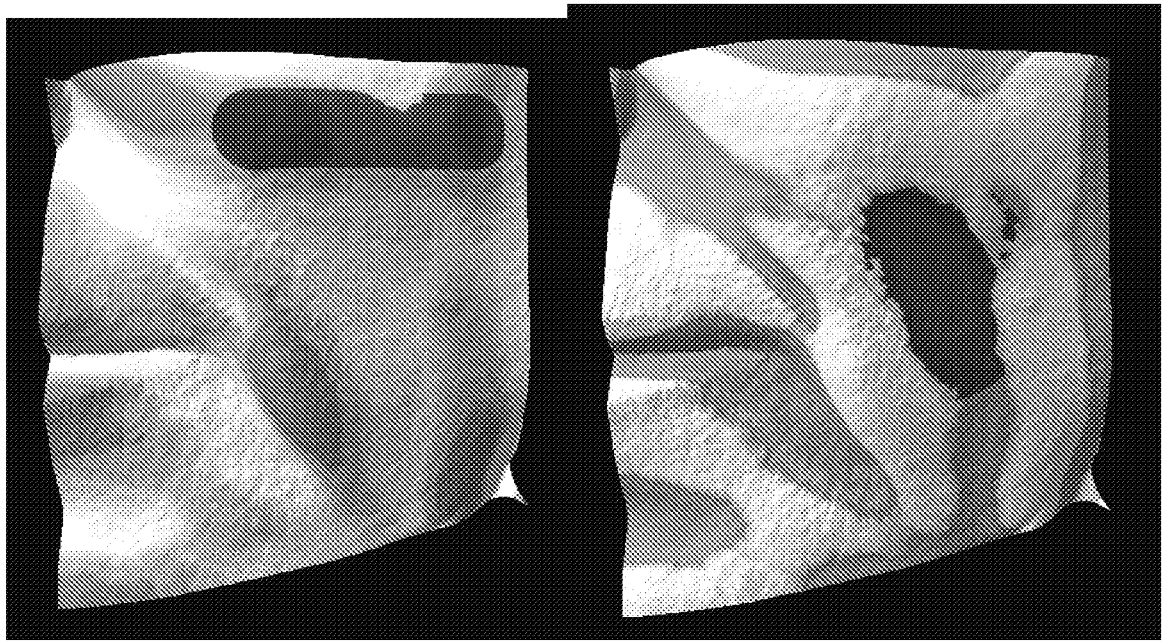
FIG. 9E      FIG. 9F
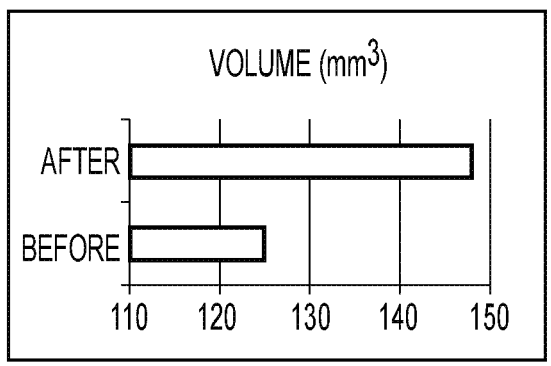
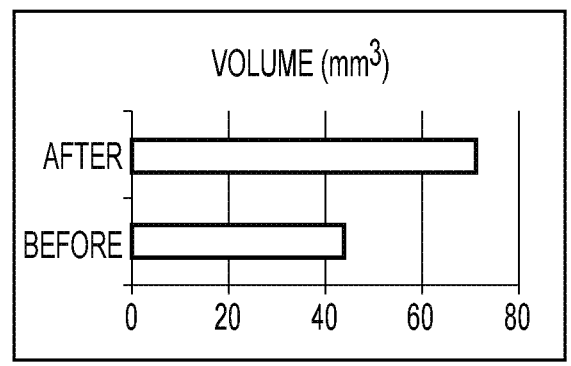
FIG. 9G      FIG. 9H

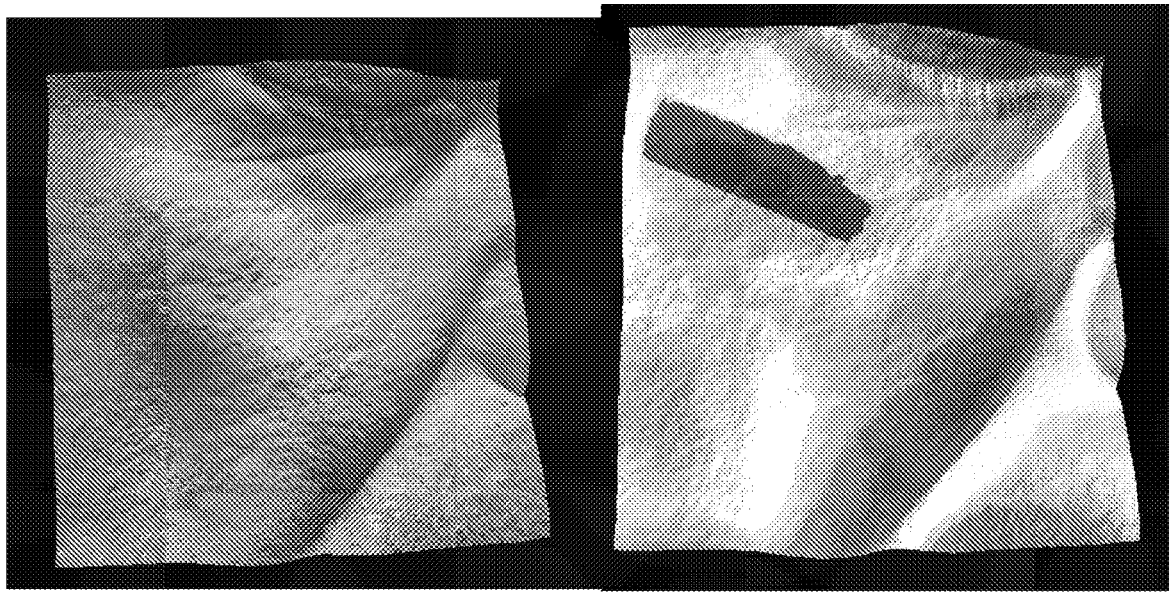
FIG. 10A  FIG. 10B
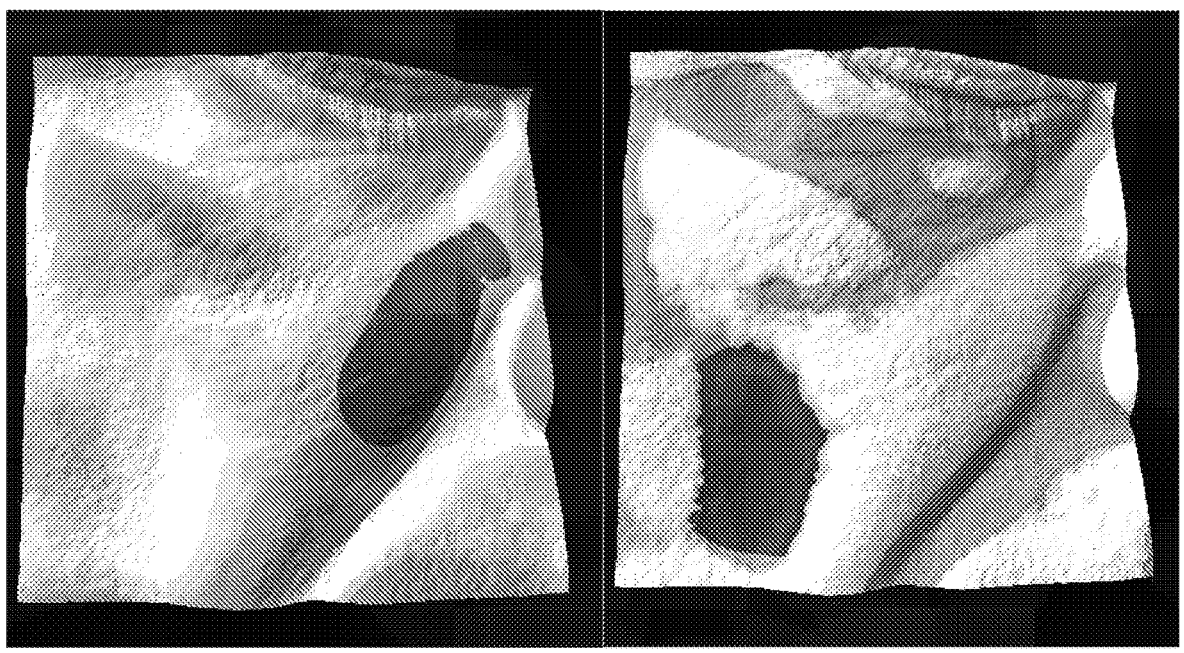
FIG. 10C  FIG. 10D

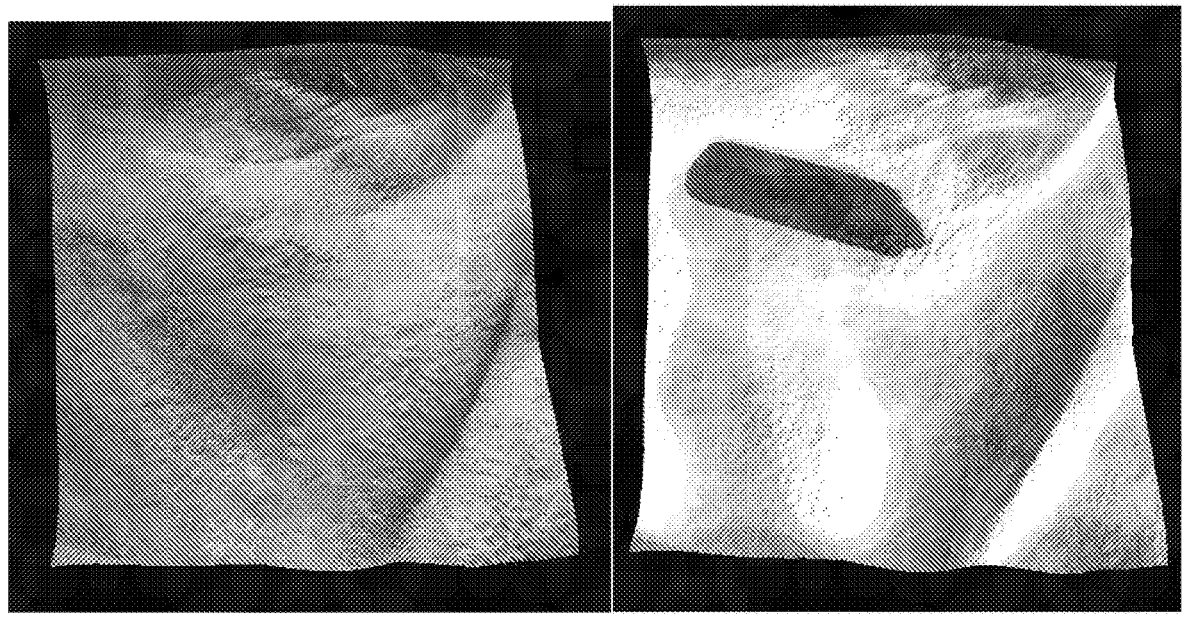
FIG. 10E  FIG. 10F
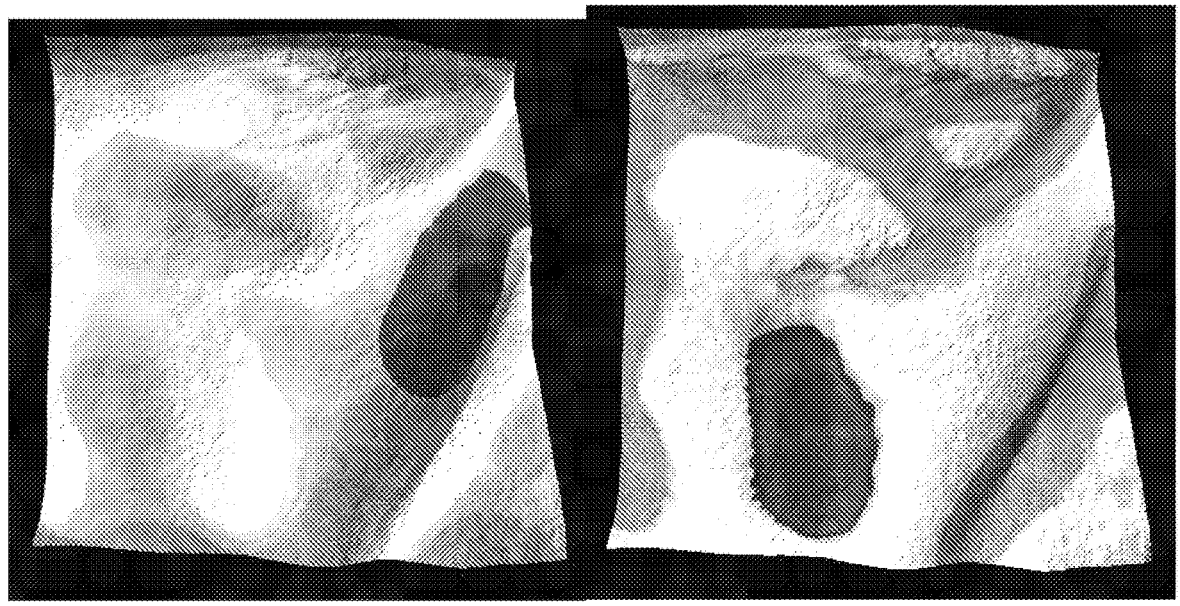
FIG. 10G  FIG. 10H

FIG. 11E  FIG. 11F
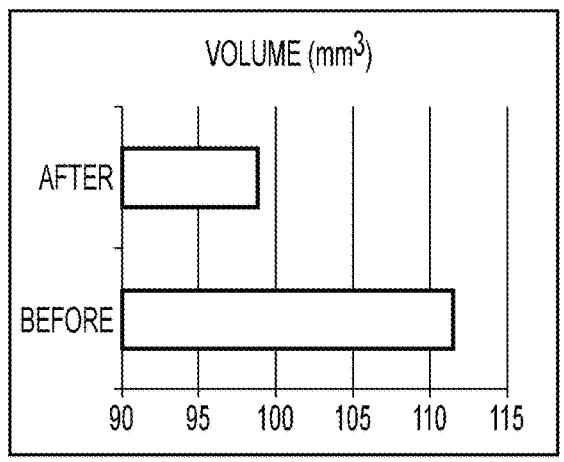 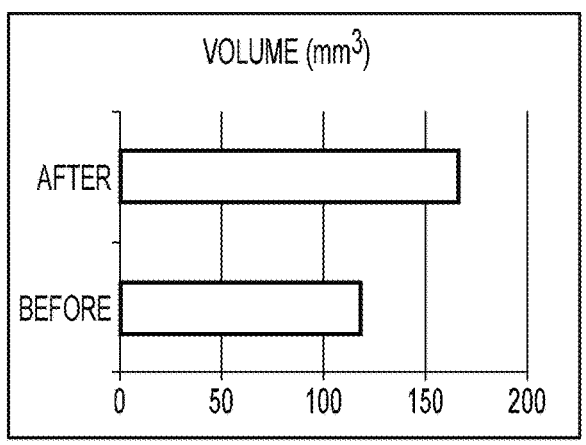
FIG. 11G  FIG. 11H

TOPICAL COMPOSITIONS AND METHODS TO PROMOTE OPTIMAL DERMAL WHITE ADIPOSE TISSUE COMPOSITION IN VIVO

CROSS REFERENCE TO RELATED APPLICATIONS

This application claims priority to and the benefit of U.S. Provisional Application No. 62/751,222, filed Oct. 26, 2018, which is expressly incorporated herein by reference in its entirety.

FIELD OF THE INVENTION

The present invention generally relates to topical compositions and methods effective for promoting an optimal dermal white adipose tissue composition in vivo comprising a promoter of adipogenesis, a lipolytic agent, and at least one penetrant.

Sun exposure and high-fat or high-carbohydrate diet can cause the loss of dermal adipocytes, which leads to the appearance of volume deficit or hollows in certain areas of the skin. Sun exposure and high-fat or high-carbohydrate diet also cause dermal adipocytes to become hypertrophic, which weakens the skin, and makes it sag. Loss of dermal adipocytes and their state of hypertrophy may occur in the same area or in adjacent areas.

Existing pharmaceutical and cosmetic approaches for promoting dermal adipogenesis do not adequately address the dual concerns of adipocyte loss and hypertrophy. These approaches focus on increasing adipocyte volume, and do not consider the potential for hypertrophy. Pharmacological agents that promote conversion of pre-adipocytes to adipocytes also generally promote lipid accumulation by the newly converted cells. Also, increasing fat cell numbers through adipogenic stimulation is more difficult and occurs more slowly than increasing fat cell size. Persistent application of pharmacological agents that promote conversion of pre-adipocytes and increase the size of adipocytes can thus initiate or exacerbate adipocyte hypertrophy.

Putative users of compositions which both promote pre-adipocyte to adipocyte conversion and accumulation of lipids by the newly converted adipocytes face two significant challenges. First, users must carefully administer the agents only to those areas of the skin that require increases in volume but not to those areas of the skin that do not. Second, users must apply the adipogenic compositions only for so long as the numbers of dermal adipocytes are insufficient or else risk unduly increasing adipocyte size to the point where hypertrophy occurs, weakens the skin and causes sagging.

The first requirement is especially difficult to fulfill with respect to the face, where areas of insufficient volume created by adipocyte loss overlap with areas containing hypertrophic adipocytes. This is especially true of the periorbital region where loss of volume in the tear trough is accompanied by sagging skin containing hypertrophic adipocytes manifesting as eye bags, but is also true of other areas of the face.

Existing pharmaceutical and cosmetic approaches seeking to improve the appearance of the skin by delivering adipogenic agents to the dermal white adipose tissue have not confronted the issue of overlapping areas of adipocyte loss and adipocyte hypertrophy. They have not been studied on the human face.

The second requirement is also difficult for users to comply with. Individuals vary with respect to the extent of their adipocyte loss. They also vary with respect to how quickly their dermal white adipose tissue will respond to treatment with adipogenic agents. Furthermore, individuals can be expected to apply different amounts of the adipogenic agents. These differences make it difficult for manufacturers to advise users on when they should stop administration.

Existing pharmaceutical and cosmetic approaches seeking to improve the appearance of the skin by delivering adipogenic agents to the dermal white adipose tissue have not confronted the issue of inducing or exacerbating adipocyte hypertrophy. These approaches have not been evaluated for long enough periods that would allow their potential for hypertrophy and resulting sagging to be assessed.

We previously reported an invention that improved the structure, function and health of dermal white adipose tissue exposed to UV damage by enhancing adipogenesis in vivo (See e.g., U.S. Provisional Application Nos. 62/555,919, filed on Sep. 8, 2017; and 62/694,723, filed Jul. 6, 2018). In that invention, we identified optional ingredients that we believed could augment adipogenesis further, by, for example, synergistically increasing PPARγ expression to amplify PPARγ signaling.

In the present invention, to our surprise, we found that an ingredient that we expected would have pro-adipogenic signaling based on its ability to increase expression of PPARγ to have the opposite effect of inducing lipolysis. More surprisingly, we found that a topical composition combining this ingredient with agents that we had shown to singularly promote adipogenesis could selectively increase adipogenesis in areas where adipogenesis was beneficial while increasing lipolysis in areas where lipolysis was beneficial. Moreover, this topical composition could be applied broadly to skin regions without selectively targeting regions requiring either adipogenesis or lipolysis.

Here, we demonstrated a method of treating deficient skin volume that addresses both the concerns of insufficient adipocyte number and excessive adipocyte size. For the first time, we showed that a composition containing a combination of agents with adipogenic and lipolytic activity effectively restores volume to those areas of the skin that require it. Moreover, this treatment improves the appearance of sagging, indicating a neutral or positive impact on adipocyte size.

Our results have been obtained in testing on the most relevant and challenging keratinic surface—the skin of the sun-exposed human face, including the most difficult peri-orbital region. We have evaluated the efficacy of our method and composition using the most meaningful instrument for assessing volume change—3D digital spectrometry. Furthermore, our testing has involved time-frames—subjects have been followed in excess of 9 months—that allow us to detect whether the resulting adipogenesis leads to unwanted gains in dermal adipocyte size that manifests as sagging.

This is the first time that it has been shown that a single topical composition can increase in vivo dermal fat volume selectively in areas of the skin, which require it while at the same time preventing excessive lipogenesis, and/or decreasing dermal fat volume where it is desirable to be reduced. Moreover, it is the first time that it has been shown that a single topical composition can promote a decrease in dermal fat volume selectively in areas of the skin where it is desirable to be reduced while at the same time preventing excessive lipolysis, and/or increasing the dermal fat volume where it is desirable to be increased. The ingredient that conferred lipolytic activity on the topical composition has been shown by others to have lipolytic activity both in vitro and in vivo with the in vitro activity being ascribed to promotion of lipase function.

SUMMARY OF THE INVENTION

In one embodiment of the invention, a topical composition effective for improving the appearance of the skin is provided, which contains at least one adipogenic agent, at least one lipolytic agent and at least one penetrant, wherein the improvement comprises an improvement in the appearance of insufficient volume. In some embodiments, the improvement in the appearance of insufficient volume occurs without causing an increase in the appearance of excess volume. In some embodiments, the improvement in the appearance of insufficient volume occurs together with an improvement in the appearance of sagging. In some embodiments, the improvement in appearance occurs in the face. In some embodiments, the improvement in insufficient volume includes an increase in volume in the periorbital area. In some embodiments, the improvement in insufficient volume includes an increase in volume along the cheekbone. In some embodiments, the improvement in insufficient volume includes an increase in volume in the upper cheek. In some embodiments, the improvement in the appearance of sagging includes a reduction in volume in the lower cheek, proximate to the nasolabial fold. In some embodiments, the improvement in the appearance of sagging includes an increase in volume of the upper cheek below the cheekbone. In some embodiments, the improvement in the appearance of sagging includes an increased volume of indentation in the mid-cheek.

In one embodiment of the invention, a topical composition effective for improving the appearance of the skin is provided, which contains at least one adipogenic agent, at least one lipolytic agent and at least one penetrant, wherein the improvement includes an improvement in the appearance of sagging.

In one embodiment of the invention, a topical composition effective for preventing damage to skin caused by sun exposure, weight gain, weight loss or physical exercise is provided, which contains at least one adipogenic agent, at least one lipolytic agent and at least one penetrant, wherein the damage to be prevented relates to decreases in dermal adipocyte numbers and their hypertrophy.

In one embodiment of the invention, a topical composition effective for increasing superficial fat volume and for decreasing superficial fat volume as needed is provided, which contains at least one adipogenic agent, at least one lipolytic agent, and at least one penetrant.

In one embodiment of the invention, a topical composition effective for selectively promoting increases or decreases in dermal fat volume as needed, which contains a mixture of a promoter of adipogenesis, a lipolytic agent and at least one penetrant.

In another embodiment of the invention, a method of promoting an optimal dermal white adipose tissue composition in an individual in need thereof is provided, wherein the method involves topically applying a composition that comprises a mixture of a promoter of adipogenesis, a lipolytic agent and at least one penetrant to a target skin region of the individual.

In one embodiment of the invention, a method of improving the appearance of the skin of an individual is provided, wherein the method involves topically applying a composition containing at least one agent possessing lipolytic activity and at least one agent possessing adipogenic activity and at least one penetrant to the skin. In some embodiments, a combination of agents possessing lipolytic and adipogenic activities is included in a single composition. In some embodiments of the invention, a lipolytic agent possessing lipolytic activity is included in a composition separately from a composition including an adipogenic agent possessing adipogenic activity. In some embodiments of the invention, the topical application of the two separate compositions occurs in close proximity in time or as part of a coordinated regiment. In other embodiments of the invention, the composition is applied to the overlapping areas of a keratin-based skin surface. In other embodiments of the invention, the composition is applied to a sun-exposed part of the body. In a preferred embodiment, the composition is applied to the face. In some embodiments of the invention, there is a visible reduction in the appearance of hollowing after applying the composition. In other embodiments of the invention, there is a visible reduction in the appearance of insufficient volume after applying the composition. In other embodiments of the invention, there is a visible reduction in the appearance of sagging or the appearance of excessive volume or both after applying the composition. In other embodiments of the invention, the improvement in skin appearance is necessitated in part by an exposure to sun, weight loss, weight gain or physical exercise. In some embodiments of the invention, there is a visible reduction in the appearance of hollowing after applying the composition in the periorbital area, in the cheekbone area and in the upper cheek area of the face. In some embodiments of the invention, there is a visible reduction in the appearance of sagging or visible improvement in the definition of the cheekbone area, the periorbital area, the upper cheek, the lower cheek or the jawline.

In one embodiment of the invention, a method of treating or preventing a defect in the appearance of the skin is provided, by employing a combination of an adipogenic agent and a lipolytic agent, where such treatment or prevention entails the use of two or more compositions separately containing lipolytic and adipogenic agents, wherein a composition containing the lipolytic and adipogenic agents may be applied to the same area of the skin.

In one embodiment of the invention, a method is provided for increasing the appearance of volume in areas of the skin where an individual requires it and for decreasing the appearance of volume in areas of the skin where the same individual requires it, the method involves topically applying a composition containing an adipogenic agent, a lipolytic agent and at least one penetrant to the skin region of the individual.

In one embodiment of the invention, a method is provided for increasing the appearance of volume in areas of the skin where an individual requires it without increasing the appearance of volume in areas of the skin where the same individual does not require it, the method involves topically applying a composition containing an adipogenic agent, a lipolytic agent and at least one penetrant to the skin region of the individual.

In another embodiment of the invention, a method is provided for decreasing the appearance of volume in areas of the skin where an individual requires it without decreasing the appearance of volume in areas of the skin where the same individual does not require it, the method involves topically applying a composition containing an adipogenic agent, a lipolytic agent and at least one penetrant to the skin region of the individual.

In one embodiment of the invention, a method for increasing the volume of adipose tissue in areas of the skin where an individual requires it and for decreasing the volume of adipose tissue in areas of the skin where the same individual requires it, the method involves topically applying a composition containing an adipogenic agent, a lipolytic agent and at least one penetrant to the skin region of the individual.

Other objects, advantages and novel features of the present invention will be readily ascertainable to persons of ordinary skill in the art. Other objects and features of the invention will be ascertainable from the following detailed description of one or more preferred embodiments when considered in conjunction with the figures presented. It should be recognized that the one or more examples in the disclosure are non-limiting examples and that the present invention is intended to encompass variations and equivalents of these examples. The disclosure is written for those skilled in the art. Although the disclosure uses terminology and acronyms that may not be familiar to the layperson, those skilled in the art will be familiar with the terminology and acronyms used herein.

BRIEF DESCRIPTION OF THE DRAWINGS

The description herein will be more fully understood in view of the following drawings.

FIG. 2 shows the before (in FIG. 2A) and after (in FIGS. 2B, 2C and 2D) photo images taken using an Antera digital camera of an individual being treated using the topical composition according to an embodiment of the invention.

FIG. 3 shows the same before (in FIG. 3A) and after (in FIGS. 3B, 3C and 3D) photo images as in FIGS. 2A, 2B, 2C and 2D, respectively. The only difference is that a different perspective has been selected.

FIG. 4 shows before (in FIGS. 4A and 4B) and after (in FIGS. 4C and 4D) photo images taken using an Antera digital camera of an individual being treated using the topical composition according to an embodiment of the invention.

FIG. 9 shows before (in FIG. 9A, FIG. 9B, and FIG. 9C) and after (in FIG. 9D, FIG. 9E, and FIG. 9F) photo images taken using an Antera digital camera of an individual being treated using the topical composition according to an embodiment of the invention. The quantification of differences between the before and after images is shown in FIG. 9G (FIG. 9B vs. FIG. 9D) and FIG. 9H (FIG. 9C vs. FIG. 9E).

DETAILED DESCRIPTION

Figure 1:
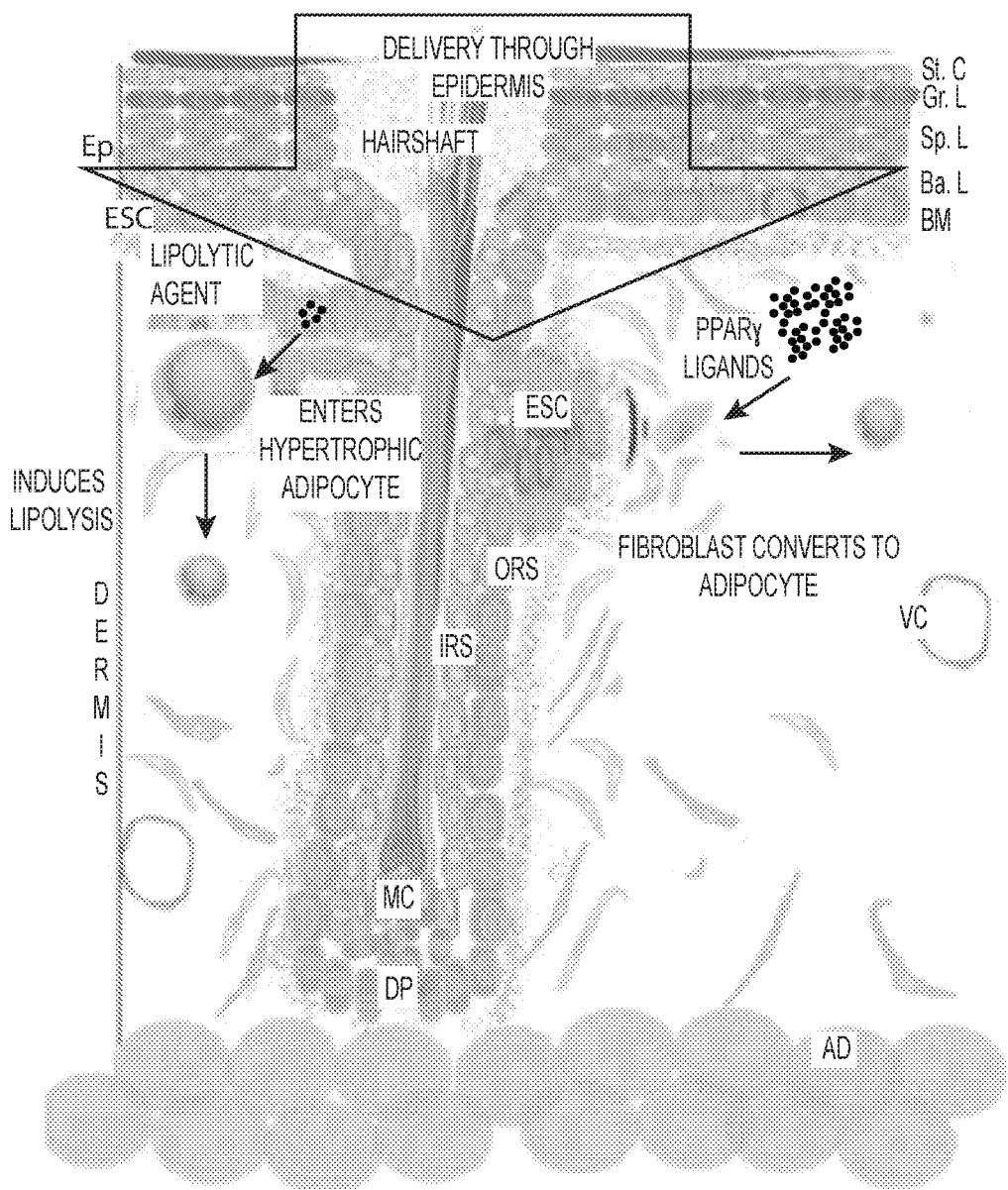
FIG. 1 illustrates the distinct skin layers of epidermis, dermis and fat in a human and a process for promoting the optimal composition of dermal white adipose tissue.
Figure 4E:
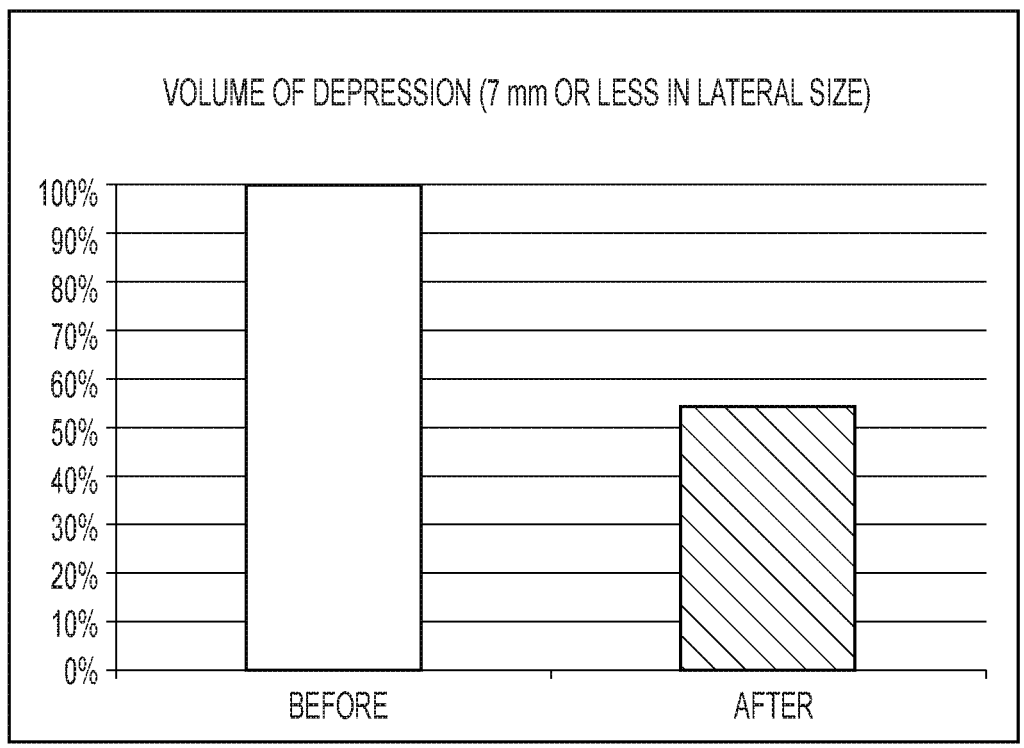
FIG. 4E is a bar graph showing the reduction in the area of skin depression.

Unless defined otherwise, all technical and scientific terms used herein have the same meaning as commonly understood by one of ordinary skill in the art to which this invention belongs.

As used herein, the terms "invention" or "present invention" are non-limiting terms and not intended to refer to any single aspect of the particular invention but encompass all possible aspects as described in the specification and the claims. As used herein, the terms "optimal" or "necessary" as used in conjunction with the term "adipogenesis" refer to the need to replenish or restore adipocyte numbers in dermal white adipose tissue exposed to UV rays causing a decrement in adipocyte numbers. As used herein, "excessive" as used in conjunction with the term lipogenesis refers to a condition of dermal white adipose tissue wherein the size of adipocytes populating said dermal white adipose tissue can be reduced.

The patent literature provides for many compositions that have been shown to promote adipogenesis or conversely to promote lipolysis in vitro.

This invention surprisingly identifies a single composition that both promotes adipogenesis and lipolysis in dermal white adipose tissue where the adipogenic and lipolytic effects of the composition do not cancel each other out. As used herein, the phrase "adipogenesis" refers to increased numbers of adipocytes resulting from conversion of cells to adipocyte lineage and/or increased differentiation of adipose-derived stem cells, as well as subsequent accumulation of lipids by these cells. As used herein, the phrase "lipolysis" refers to the reduction of lipid stores in mature adipocytes. As used herein, the phrase "lipogenesis" refers to the accumulation of lipid stores in adipocytes. For the first time, it is shown that a single composition can promote context-specific adipogenesis and lipolysis. Using 3D photography over an extended time period, it is shown that adipogenesis and lipolysis are discretely effected in adjacent areas of dermal white adipose tissue.

Compositions

In one aspect, the present disclosure is directed to topical compositions effective for promoting in vivo adipogenesis and inducing lipolysis in dermal white adipose tissue comprising an active ingredient with adipogenic activity and an active ingredient with lipolytic activity and at least one penetrant.

In another aspect, the invention employs penetrants to deliver the ingredients with adipogenic and lipolytic activity through the epidermis into skin in a manner effective to achieve a safe and effective dose. As used herein, "safe and effective dose" is intended to mean that amount of the instant composition which is sufficient to either: (i) ameliorate one or more symptoms of a disease or (ii) produce one or more positive desirable cosmetic effects. Further, the instant composition when topically applied is not painful: it does not elicit irritation, a skin reaction, inflammation or an allergic reaction. As used herein, "penetrant" is intended to refer to an agent that promotes skin penetration. As the composition reaches the dermis, the adipogenic ingredients enter resident pre-adipocyte cells and are conveyed to cell nuclei where they signal through peroxisome proliferator-activated receptor gamma (PPARγ) to induce conversion of cells to adipocyte lineage; upon entering the dermis the lipolytic ingredients enter resident mature adipocytes and cause them to release lipids. PPARγ is known to regulate fatty acid storage and glucose metabolism. PPARγ is also known to regulate differentiation of adipocytes. The lipolytic ingredients enter adipocytes and stimulate intracellular lipases to degrade triaglycerol stores and release of fatty acids. Two prominent intracellular lipases are Adipose Triglyceride Lipase and Hormone-sensitive Lipase. These lipases are subject to regulation by hormones and chemical agents.

FIG. 1 illustrates the distinct skin layers of epidermis, dermis and subcutis in a human. Also illustrated in FIG. 1, the process for promoting the structure and function of dermal white adipose tissue (dWAT) starts with delivering the composition of the invention to PPARγ receptor ligands through the dermis. The dermis is composed of three major types of cells: fibroblasts, macrophages, and adipocytes. The PPARγ receptor ligands then signal pre-adipocytes to be converted to adipocytes. The newly converted adipocytes restore the sub-dermal white adipose tissue that may be lost due to sun exposure or weight gain.

In one preferred embodiment of the invention, the adipogenic ingredient comprises unsaturated fatty acids selected from the group consisting of $C_{18:1}$, $C_{18:2}$, $C_{18:3}$, $C_{18:4}$, $C_{20:1}$, $C_{20:3}$, $C_{20:4}$, $C_{20:5}$, $C_{22:1}$, $C_{22:4}$, $C_{22:6}$, $C_{24:1}$, and unsaturated derivatives and mixtures thereof. As defined herein, fatty acids are described by their total number of carbon atoms (in subscript) followed by the total number of double bonds. For example, "$C_{18:1}$ fatty acid" is intended to mean a $C_{18}$ fatty acid having one double bond, for example, but not limited to, oleic acid. "$C_{18:2}$ fatty acid" is intended to mean a $C_{18}$ fatty acid having two double bonds, for example, but not limited to, linoleic acid. "Unsaturated fatty acids" refers to a fatty acid in which there is one or more double bonds in the fatty acid chain, including monounsaturated and polyunsaturated fatty acids. For example, "unsaturated $C_{18}$ fatty acids" could mean one or more $C_{18}$ fatty acids selected from the group consisting of oleic acid, linoleic acid, α-linolenic acid, γ-linolenic acid, conjugated linoleic acid and isomers thereof. In other preferred embodiments of the invention, the unsaturated $C_{18}$ and $C_{24}$ fatty acids could be selected from the group consisting of oleic acid, linoleic acid, α-linolenic acid, γ-linolenic acid, dihomo-γ-linolenic acid, arachidonic acid, stearidonic acid, eicosapentaenoic acid, docosahexaenoic acid, dihomo-γ-linolenic acid, docosatetraenoic acid, vaccenic acid, paullinic acid, elaidic acid, gondoic acid, erucic acid, nervonic acid, and derivatives and mixtures thereof. In other preferred embodiments, the topical composition of the invention can include naturally occurring unsaturated fatty acids, for example those selected from the group consisting of sunflower seed oil, grape seed oil, kukui oil, canola oil, evening primrose oil, chia oil, hemp oil, wheat germ oil, soybean oil, sesame oil, borage oil, blackcurrant oil, cottonseed oil, safflower oil, corn oil, and mixtures thereof. In other preferred embodiments, the adipogenic ingredient can include a medicinal plant, for example, an extract of *Kaempferia parviflora*.

In one preferred embodiment of the invention, the adipogenic agent is selected from the group consisting of: Aculeatin, Ascorbic acid, Black soybean extract, Chlorogenic acid, *Cinnamomum cassia* extract, *Cinnamomum zeylanicum* extract, Cinnamtannin B1, *Citrus aurantium* L. extract, *Lomatium suksdorfii* extract, Melatonin, Phytol, Sinensetin, Suksdorfin, *Syzygium aqueum* leaf extract and *Toddalia asiatica* (L.) lam. extract.

In one preferred embodiment of the invention, the adipogenic agent is selected from the group consisting of: (2S)-7,4'-dihydroxy-8-prenylflavan, *Morus yunnanensis* extract, 3-Butylated hydroxyanisole, 4-methoxychalcone, *Anemarrhena asphodeloides* extract, *Artemisia santolinifolia* extract, *Artemisia scoparia*, Bavachin, *Dodonaea viscosa* extract, *Miconia* sp. extract, *Piper chaba* fruit extract, Phloretin, *Psoralea corylifolia* L. fruit extract, Sage extract, Sakuranetin, Sarsapogenin, *Rubus suavissimus* extract and Vanadium.

In one preferred embodiment of the invention, the adipogenic agent is selected from the group consisting of: 10-oxo-12(Z)-octadecenoic acid, 13-Oxo-9(Z), 11(E), 15(Z)-octadecatrienoic acid, 15-(S)-hydroxyeicosatetraenoic acid, Acrylamide, *Bidens* extract, Brazilian red propolis extract, Butylated hydroxyanisole, Chebulagic acid, *Chlorella vulgaris* extract, *Cirsium japonicum* extract, Cyanidin-3-glucoside, Daidzein, Diallyl disulfide, *Echinacea purpurea* root extract, Emodin, Flavanone, Furan Fatty Acid 9M5, Geranylgeraniol, Ginsenoside 20S-protopanaxatriol, Ginsenoside Rb1, Ginsenoside Re, Ginsenoside Rh2, Glabridin, *Heracleum dissectum* Lebb extract, Hydrogen sulfide, *Illicium anisatum* extract, *Inonotus obliquus* extract, Isoimperatorin, Lactate, Lecithin, Licorice extract, *Lolium multiflorum* extract, *Moringa concanensis* nimmo extract, N-Oleoyl glycine, *N. nouchali* seed extract, Norwogonin, *Notopterygium incisum* root extract, Palmitoyl lactic acid, Pentamethylquercetin, Phenyllactic Acid, Quinine, Retrofractamide A, *Rheum palmatum* L rhizome, S-adenosylmethionine, Sangennol F, *Sargassum yezoense* extract, Soy pinitol, Spermidine, Techtochrysin, *Terminalia chebula* fruit extract, *Tetracera indica* merr. extract, Tetramethylkaempferol, Umbelliferone, *Undaria* extract, Vitamin B3 and Vitamin B6.

In one preferred embodiment of the invention, the lipolytic ingredient comprises a medicinal plant, for example, an extract of *Kaempferia parviflora*.

In one preferred embodiment of the invention, the lipolytic agent is selected from the group consisting of: Ascorbic acid, Butyrate, *Chrysanthemum* extract, Chlorogenic acid, *Citrus aurantium* extract, Eicosapentaenoic Acid, Gallic acid, Hydrocortisone, Hydrocortisone acetate, Hydrocortisone butyrate, INDUS810, *Kaempforia parviflora* extract, Lycopene, Magnolol, *Magnolia* bark extract, *Morus bombycis* extract, *Pueraria lobata* root extract, Resveratrol, *Schisandra chinensis* extract, Sodium butyrate, *Solenostemma argel* extract, *Syzygium aqueum* extract, *T. foenum graecum* seed extract, Triphenyl phosphate and Tyramine.

In one preferred embodiment of the invention, the lipolytic agent is selected from the group consisting of: 3-Iodothyronamine, *Aegle marmelos* leaf extract, *Anoectochilus formosanus* extract, Arginine, *Brucea javanica* extract, Brucein A, Brucein B, Brucein C, 3'-hydroxybrucein A, Brusatol, Bruceantinol, *Cassia tora* seed extract, *Centella asiatica* leaf extract, Chinese olive extract, *Cyclopia maculata* extract, Fermented *Castanea crenata* inner shell extract, Forskolin, *Gardinia fructus* extract, Genipin, *Hemerocallis fulva* extract, *Juglans mandshurica* maxim extract, Licarin A, Lychee fruit extract, Magnesium, Malic acid, Okadaic acid, *Paecilomyces hepiali* mycelia extract, Palmitoleic acid, *Phaseolus vulgaris* extract, *Posidonia oceanica* (L.) delile Extract, *Salacia* (S.) *reticulata* extract, Sea cucumber saponin echinoside A, *Smilax china* L. leaf extract, Soy hydrolysate, Soyasapogenol A, Soyasapogenol B, Octopamine, N-methyltyramine, *Syzygium cumini* (L.) skeels, TAT-glycine-lysine-histidine complex, *Terminalia sericea* extract, *Toona sinensis* extract, and *Zanthoxylum schinifolium* seed oil.

In one preferred embodiment of the invention, the lipolytic agent is selected from the group consisting of: Acetyl-keto-β-boswellic acid, Aged black garlic extract, Almond skin extract, Andiroba extract, Apigenin, Apple extract, *Artemisia sacrorum* ledeb. extract, *Astilbe chinensis* Franch. et Savet. extract, *B. platyphylla* bark, B. platyphylloside, Berberine, Bergamottin, Betulinic acid, Bilobilide, Black adzuki bean extract, Black tea extract, *Brassica campestris* spp. *rapa* root extract, Caffeine, Capsanthin, *Capsicum annum* L. seed oil, Capsaicin, Carnitine, Chitosan, Chrysophanol, Cinnamaldehyde, Cirsimarin, *Cirsium* setidens nakai extract, *Citrus bergamia* extract, *Citrus* unshu mark extract, Clove extract, Coffee extract, *Commiphora mukul*, Crocin, *Cucurbita moschata* extract, Curcumin *longa* extract, *Cyclopia intermedia*, Epigallocatechin gallate, *Euglena*, Eurycomanone, *Eurycoma longifolia* extract, Fucoidan, Fucoxanthin, *Fucus vesiculosus* extract, *Garcinia gummi-gutta* extract, *Gelidium amansii* extract, Genistein, Germinated soybean protein hydrolysate, *Gingko biloba* extract, Ginsenoside Rg1, Gomisin, Grape seed extract, Grape skin extract, Green tea extract, *Humulus japonicas*, Hydroxytyrosol, Hydroxysafflor yellow A, Isopropylnorsynephrine, Kaempferol, Korean Chungtaej eon tea extract, Lipoic acid, Lotus leaf extract, Lotus seed extract, Luteolin, *Lysimachia foenum-graecum* extract *Moringa* seed extract, Morusin, *Musa sapientum* pulp extract, Myricanol, Naringenin-7-O-glucoside, New Zealand black currant extract, Oleanolic acid, Oleoresin *capsicum*, Oleuropein, P-synephrine, Pear pomace extract, Plum extract, *Polygonum fagopyrum*, Pterostilbene, Pycnogenol, Quercetin, Quinic acid, Rasberry ketone, *Rubus fructicosus* extract, Purple sweet potato extract, Rutin, *Salvia miltiorrhiza* extract, Sericoside, Sinensetin, Spilanthol, Stem bromelain extract, Sun *ginseng* extract, Synephrine, Syringic acid, Tanshinone IIA, *Taraxacum officinale* extract, Triamcinolone Acetonide, Ursolic acid, Vitamin D, Widdrol, Xanthigen, and Xanthohumol.

In one preferred embodiment of the invention, the topical composition of the invention includes from about 5% (w/w) to about 40% (w/w), preferably from about 10% (w/w) to about 30% (w/w) of a source of unsaturated fatty acids whose carbon chains are principally (e.g., more than 30% of total) of carbon chain lengths 18 or higher. The abbreviation "(w/w)", as used herein, means the true percentage by weight. That is, the weight of the ingredient is divided by the total weight of the composition and converted to a percentage.

In some embodiments, the topical composition of the invention includes from about 5% (w/w) to about 40% (w/w), preferably from about 10% (w/w) to about 30% (w/w) of a source of unsaturated fatty acids whose carbon chains are principally (e.g., more than 30% of total) of carbon chain lengths 18 or higher. The abbreviation "(w/w)", as used herein, means the true percentage by weight. That is, the weight of the ingredient is divided by the total weight of the composition and converted to a percentage.

In one preferred embodiment of the invention, the penetrant or penetrants is/are selected from the group consisting of urea, imidurea, palmitate, isopropyl palmitate, isoproyl myristate, propylene glycol, and nonionic detergents.

In some embodiments, the topical composition of the invention includes from about 5% (w/w) to 25% (w/w), preferably from about 7% (w/w) to 15% (w/w) of a penetrant or penetrants.

In some embodiments, the topical composition of the invention optionally may include from about 0.1% (w/w) to about 25% (w/w), preferably from about 0.1% (w/w) to about 5% (w/w) of hyaluronic acid. More preferably, from about 0.1% (w/w) to 1.0% (w/w). Hyaluronic acid is a naturally occurring glycosaminoglycan distributed widely throughout a person's connective, epithelial, and neural tissues. It is known for its water-binding and water-attracting attributes which fill up the spaces between the connective fibers collagen and elastin in the dermis. Its molecular weight may vary from 50,000 Daltons upwards, and it forms highly viscous solutions. In one embodiment of the invention, a form of hyaluronic acid is selected from the group consisting of hyaluronic acid including its salts, analogs, modifications, and derivatives thereof. In one embodiment, the form of hyaluronic acid is sodium hyaluronate or potassium hyaluronate. Potassium and sodium hyaluronate are water soluble salt forms of hyaluronic acid.

In one embodiment of the invention, the weight percentages of adipogenic agent present in the topical composition is greater than the weight percentages of lipolytic agent present in the topical composition.

In some embodiments of the invention, the topical composition further includes an agent with indirect adipogenic activity. In some embodiments of the invention, the topical composition further includes an agent with indirect lipolytic activity.

The topical compositions described herein can further include additional ingredients and other optional ingredients known to be useful in personal care formulations.

Generally, the topical compositions include a carrier.

In some embodiments, the topical compositions are liquid compositions desirably containing water as the carrier. Suitable amounts of water can be from about 0.1% by weight of the composition to about 99.9% by weight of the composition. More typically, the amount of water can be from about 40% by weight of the composition to about 99.9% by weight of the composition. Preferably, the amount of water can be from about 60% by weight of the composition to about 99.9% by weight of the composition.

In another embodiment, the topical composition includes at least one active ingredient and a hydrophobic carrier. Suitable hydrophobic carriers can be, for example, natural oils, synthetic oils, and combinations thereof. Other hydrophobic carriers would be known to person of ordinary skill in the art.

The topical compositions can further include a skin soothing agent. As used herein, "skin soothing agent" refers to compounds that reduce or prevent skin irritation. Suitable skin soothing agents can be, for example, botanical extracts such as calendula, chamomile, aloe, comfrey, coneflower; active materials such as allantoin, bisabolol, panthenol, beta-glucan, colloidal oatmeal, and ingredient blends such as SymCalmin® (including e.g., butylene glycol, pentylene glycol, and hydroxyphenyl propamidobenzoic acid); commercially available from Symrise and SEPICALM™ (including e.g., sodium palmitoyl proline, *Nymphaea alba* flower extract (commercially available from Seppic)).

The topical compositions can further include a humectant. Humectants can elevate the hydration of the skin, in particular the epidermis and the dermis. Suitable humectants can be, for example, glycerol, glycerin, lactic acid, urea, aloe vera, betaine, propanediol, propylene glycol, butylene glycol, and combinations thereof.

The topical compositions can further include an emulsifier, and in particular, an emulsifier that creates liquid crystalline networks or liposomal networks. Suitable non-limiting exemplary emulsifiers include, for example, OLIVEM® 1000 (including e.g., Cetearyl Olivate and Sorbitan Olivate (commercially available from HallStar Company)), Arlacer™ LC (including e.g., Sorbitan Stearate and Sorbityl Laurate (commercially available from Croda)), CRYSTALCAST® MM (including e.g., Beta Sitosterol, Sucrose Stearate, Sucrose Distearate, Cetyl Alcohol, Stearyl Alcohol (commercially available from MMP Inc.)), UNIOX CRISTAL (including e.g., Cetearyl Alcohol, Polysorbate 60, Cetearyl Glucoside (commercially available from Chemyunion)). Other suitable emulsifiers include lecithin, hydrogenated lecithin, lysolecithin, phosphatidylcholine, phospholipids, and combinations thereof. In a preferred embodiment, the topical composition includes emulsifiers derived from cellulose, such as methylcellulose, hydroxyethylcellulose, hydroxypropyl methylcellulose and mixture thereof. Suitable amounts of emulsifiers can be from about 0.4% to about 1.75% by weight of the composition.

Additionally, the topical compositions can also include triethanolamine (TEA), diethanolamine (DEA) and ethanolamine, which are commonly used to help form emulsions. Suitable amounts of triethanolamine (TEA), diethanolamine (DEA) or ethanolamine added can be from about 0.4% to about 1.75% by weight of the composition.

The topical compositions can further include cross-linked polyacrylate polymers such as Carbomer® 934, Carbomer® 940, Carbomer® 980, Carbomer® 990, and Carbomer® 996, which served as emulsion stabilizer or as viscosity increasing agent. Suitable amounts of cross-linked polyacrylate polymers can be from about 0.5% to about 5% by weight of the composition.

The topical compositions can further include a preservative to preserve the stability. Preservatives can also prevent the growth of microbial organisms in the compositions. Suitable preservatives are known in the art, and include, for example, methylparaben, phenoxyethanol, capryl glycol, glyceryl caprylate, benzoic acid, sorbic acid, gallic acid, propylparaben, butylated hydroxytoluene (BHT), oxyprotect, Euxyl® products and combinations thereof. Other suitable preservatives would be known to a person of ordinary skill in the art. Suitable amounts of preservatives can be from about 0% to about 7% by weight of the composition.

The topical compositions can further include a pH adjuster to control/maintain the pH of the composition within the range of skin pH.

The topical compositions can further include fragrances, scents, dyes, surfactants, emollients, antioxidants, rheology modifiers, film formers and other components known to be useful in personal care formulations. Suitable surfactants can be, for example, Brij® 20, Brij® 28, Brij® 98, Brij® 99. Suitable amounts of surfactants can be from about 0.25% by weight of the composition to about 1% by weight of the composition. Suitable emollients can be, for example, an alcohol-based emollient such as isopropyl palmitate or isopropyl myristate. Suitable amounts of emollient can be from about 1% by weight of the composition to about 7% by weight of the composition.

Methods of Use

In another aspect, the present disclosure is directed to methods of modulating the structure, function, and health of dermal white adipose tissue in an individual in need thereof, the method comprising the steps of: topically applying a composition that comprises an adipogenic ingredient, a lipolytic ingredient and at least one penetrant to a target skin region of the individual. The targeted skin region is not limited to a discrete region that requires adipogenesis or conversely lipolysis but rather the composition can be administered to broad areas of the skin incorporating both areas that are in need of adipogenesis and areas that are in need of lipolysis.

In another aspect, the present disclosure is directed to methods of effecting an increase in adipogenesis to a discrete region of the skin in an individual in need thereof without effecting a global increase in adipogenesis, comprising topically applying a composition that comprises an adipogenic ingredient, a lipolytic ingredient and at least one penetrant.

In another aspect, the present disclosure is directed to methods of effecting an increase in lipolysis in a discrete region of the skin in an individual in need thereof without effecting a global increase in lipolysis, comprising topically applying a composition that comprises an adipogenic ingredient, a lipolytic ingredient and at least one penetrant.

The topical compositions can be applied to the target skin region by any suitable delivery vehicle. For example, the composition can be applied as a lotion, as a wash, as a gel, as a salve, as an ointment, as a cream, as a solid stick, and/or as a foam. Additionally, the composition can be applied with a wipe, with mitts and gloves, using an aerosol dispenser, using a pump spray, using a trigger spray, using a squeeze bottle, and/or a mask.

The compositions can be applied daily, every other day, every couple of days, every week, every month, and every year, as desired. The compositions can be applied multiple times per day, multiple times per week and/or multiple times per month. In one embodiment, the composition is applied regularly for at least six weeks. In another embodiment, the composition is applied at least twice per day.

In some embodiments, the compositions of the present disclosure can be used with additional skin care compositions as part of a skin care regimen. For example, in facial treatment and care. In the present disclosure, it should be understood that at least one of the products of the regime includes the topical composition of the present disclosure, thereby providing the benefit of promoting the structure and function of dermal white adipose tissue.

It should be understood by a skilled artisan that, while skin care systems will be discussed herein, regimes using the compositions of the present disclosure can be used for various other daily regimens comprising steps to cleanse, treat, moisturize, and protect the skin. It is understood that skin care regimens can combine all of these steps, some of these steps, or have multiple iterations of the same steps so as to provide desired benefits to the skin.

Other objects, advantages and novel features of the present invention are apparent from the foregoing detailed description of the one or more preferred embodiments, examples and aspects. It should be recognized that the one or more examples in the disclosure are non-limiting examples and that the present invention is intended to encompass variations and equivalents of these examples.

EXAMPLES

Example 1

Preparation for a topical composition according to an embodiment of the invention.

Various components in accordance with the amounts shown in Table 1 were uniformly dispersed and dissolved to obtain the composition and then stirred to obtain a lotion.

TABLE 1

| Ingredients | Grade | Amount (g) |
|---|---|---|
| Water | USP | 60-70 |
| Cross linked polyacrylate polymer such as Carbomer 934, Carbomer 940, Carbomer 980, Carbomer 990, and Carbomer 996. | USP | 0.5-5 |
| Emulsifier derived from cellulose such as, methylcellulose, hydroxyethylcellulose, or hydroxypropyl methylcellulose or mixture thereof. | USP | 0.4 to 1.75 |
| pH adjuster such as natrium sodium. | | 0.01 to 0.05 |
| Oil rich in C18 polyunsaturated fatty acids such as sunflower seed oil, grape seed oil, kukui oil, canola oil, evening primrose oil, chia oil, hemp oil, wheat germ oil, soybean oil, sesame oil, borage oil, blackcurrant oil, cottonseed oil, safflower oil, and corn oil or mixtures thereof. | USP | 15-25 |
| A lipolytic agent such as extract of kaempferia parviflora | USP | 0.1 to 7 |
| A caprylyl alcohol-based emollient such as dicaprylyl carbonate or dicaprylyl maleate. | USP | 1-7 |
| Skin penetrant such as propylene glycol, butylene glycol, azone, or urea. | USP | 4-10 |
| Surfactant such as Brij 020, Brij 28, Brij 98, and Brij 99. | USP | 0.25 to 1 |
| Vitamin E | USP | 0.25 to 1 |
| Hyaluronic acid | USP | 0.1 to 1 |
| Preservative such as Oxyprotect. | USP | 0.01 to 0.1 |
| Preservative such as Euxyl. | USP | 0.01 to 0.1 |
| Fragrance | USP | 0.25 to 1 |
| Total | | 100 |

Example 2

FIGS. 2A, 2B, 2C and 2D show before and after photo images of an individual being treated using the topical composition according to the invention. The topical composition according to the invention was applied to a broad region starting under the right eye and extending down the cheek to the right corner of the mouth. The treatment period lasted seventy four days with application no less frequent than twice per day. Photos were taken with an Antera digital camera system that creates its own light source and does not depend on natural light. No manipulation of the images was done. The increase in adipogenesis is reflected in the resolution of a discrete depression in the upper left corner of the right cheek. This depression decreases in appearance at 29 days of use (FIG. 2B in comparison to FIG. 2A). There is a further decrease in appearance of this depression after 40 days of use (FIG. 2C in comparison to FIG. 2B). The improvement in appearance of the depression is maintained at 74 days of use (FIG. 2D in comparison to FIG. 2B).

Example 3

FIGS. 3A, 3B, 3C and 3D are the same exact photo images as FIGS. 2A, 2B, 2C and 2D but shown from a different perspective, specifically depicting the profile of the check as viewed from the side of the head looking inward toward the nose. The Antera 3D digital camera system allows the user to select any perspective of a captured image by rotating and tilting the image. FIG. 3B shows the increase in volume at the discrete depression depicted in FIG. 2B and a general puffier appearance of the cheek profile compared to FIG. 3A. FIG. 3C shows a sleeker cheek profile compared to FIG. 3B. FIG. 3D shows a distinctly different contour of the cheek profile compared to FIG. 3C.

Example 4

FIGS. 4A, 4B, 4C and 4D show before and after photo images of the individual depicted in FIGS. 2A, 2B, 2C and 2D. Before photos (FIG. 4A in natural mode and FIG. 4B in very large depression mode) depict the periorbital right eye region prior to the individual starting treatment using the topical composition according to the invention. The topical composition was applied for 85 days. Photos were taken with an Antera 3D camera (which generates its own consistent light source and automatically compares the same selection across multiple images). Depression depth is quantified and represented topographically by color, ranging from white (no depression) to yellow, green, blue and purple (maximum depression). No manipulation of the images was done. The images (See FIG. 4D in comparison to FIG. 4B) captured with an Antera 3D camera show a 46% reduction in volume ($mm^3$) of skin depressions of 7 mm or less in lateral size as reported in the bar graph depicted in FIG. 4E. The Antera 3D camera system categorizes depressions of 7 mm or less in lateral size as "very large." FIGS. 4A, 4B, 4C, and 4D show that volume in the periorbital region of the right eye increased (e.g., area of depression decreasing) while volume along the cheek profile depicted in FIGS. 3A, 3B, 3C and 3D selectively decreased.

Example 5

Figures 5A, 5B:
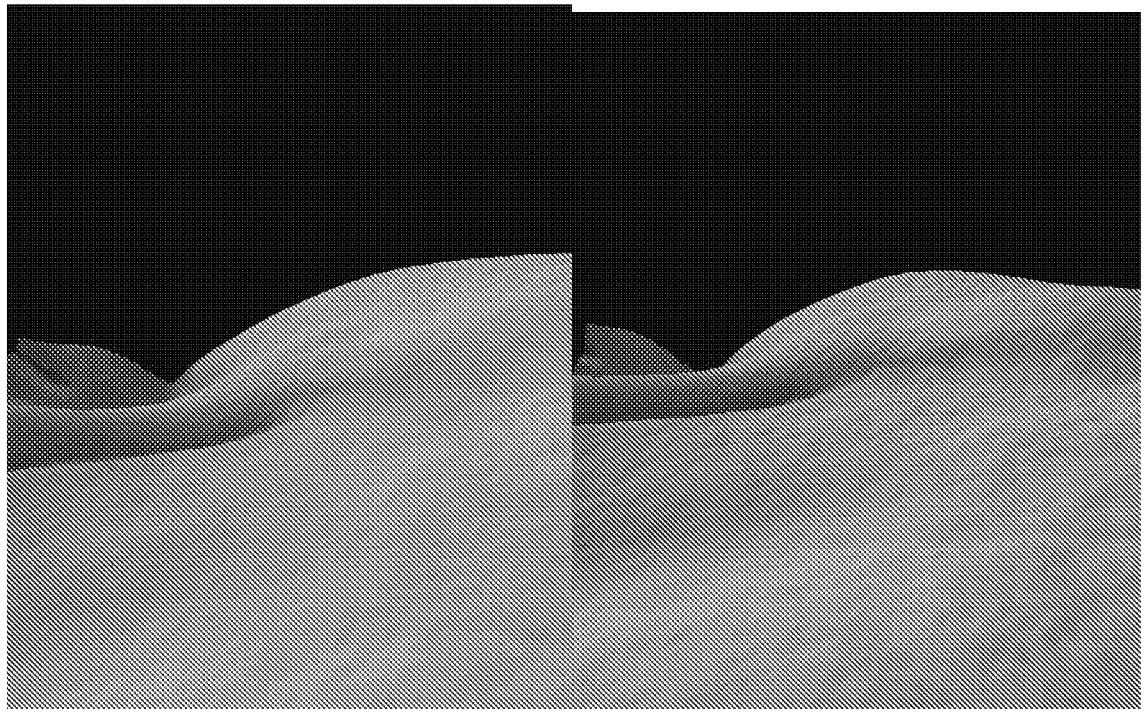
FIG. 5 shows before (in FIG. 5A) and after (in FIG. 5B) photo images taken using an Antera digital camera of an individual being treated using the topical composition according to an embodiment of the invention.

FIGS. 5A and 5B show before and after photo images of an individual being treated using the topical composition according to the invention. The topical composition according to the invention was applied to the left cheek area. The treatment period lasted approximately 4 months with application no less frequent than twice per day. The profile of the left cheek is shown from the perspective of the chin looking upward toward the left side of the head. Photos were taken with an Antera 3D digital camera system. No manipulation of the images was done. The volume of the left cheek appears significantly diminished in FIG. 5B compared to 5A, with the resulting profile far sleeker.

Example 6

Figures 6A, 6B:
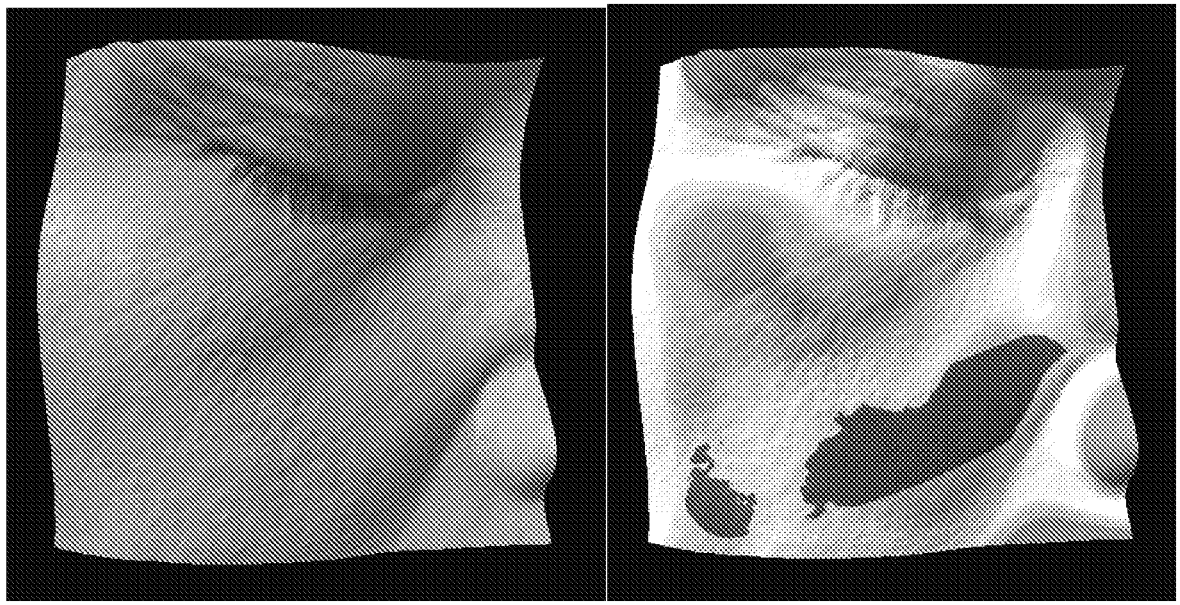
FIG. 6 shows before (in FIG. 6A, FIG. 6B, and FIG. 6C) and after (in FIG. 6D, FIG. 6E, and FIG. 6F) photo images taken using an Antera digital camera of an individual being treated using the topical composition according to an embodiment of the invention. The quantification of differences between the before and after images is shown in FIG. 6G (FIG. 6B vs.
FIG. 6E) and FIG. 6H (FIG. 6C vs.
FIG. 6F).
Figure 6C:

FIGS. 6A-6C and 6D-6F show before and after photo images, respectively, of an individual being treated using the topical composition according to the invention. The topical composition according to the invention was applied to the right side of the face. The treatment period lasted 199 days with application no less frequent than once per day. FIGS. 6A and 6D show the before and after photo images. FIGS. 6B and 6E show before and after images of the lower cheek area topographically with areas of elevation appearing darker and with a highlighted portion selected for quantification. FIG. 6G shows a graph comparing the volume in the highlighted sections of the lower cheek area in FIGS. 6B and 6E in cubic millimeters as computed automatically by the Antera system. The treatment resulted in a 14% decrease in volume in the lower cheek and represents a significant improvement in the appearance of sagging. FIGS. 6C and 6F show before and after images of cheekbone area topographically with areas of elevation appearing darker and with a highlighted portion selected for quantification. FIG. 6H shows a graph comparing the volume in the highlighted sections of FIGS. 6C and 6F in cubic millimeters as computed automatically by the Antera system. The treatment resulted in a 14% increase in volume in the highlighted area and represents a significant improvement in the appearance of cheekbone elevation and definition.

Example 7

Figures 7E, 7F:
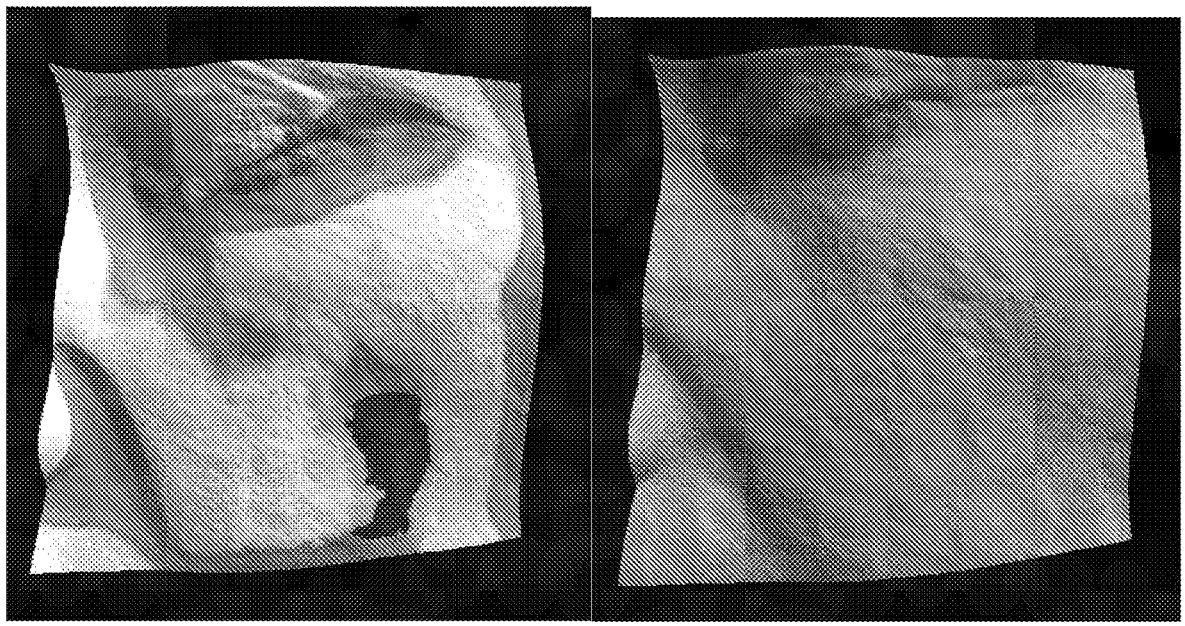
FIG. 7 shows before (in FIG. 7A, FIG. 7B, FIG. 7C, FIG. 7D, and FIG. 7E) and after (in FIG. 7F, FIG. 7G, FIG. 7H, FIG. 7I and FIG. 7J) photo images taken using an Antera digital camera of an individual being treated using the topical composition according to an embodiment of the invention. The quantification of differences between the before and after images is shown in FIG. 7K (FIG. 7B vs.
FIG. 7G), FIG. 7L (FIG. 7C vs.
FIG. 7H), FIG. 7M (FIG. 7D vs.
FIG. 7I) and in FIG. 7N (FIG. 7E vs.
FIG. 7J).
Figures 7G, 7H:
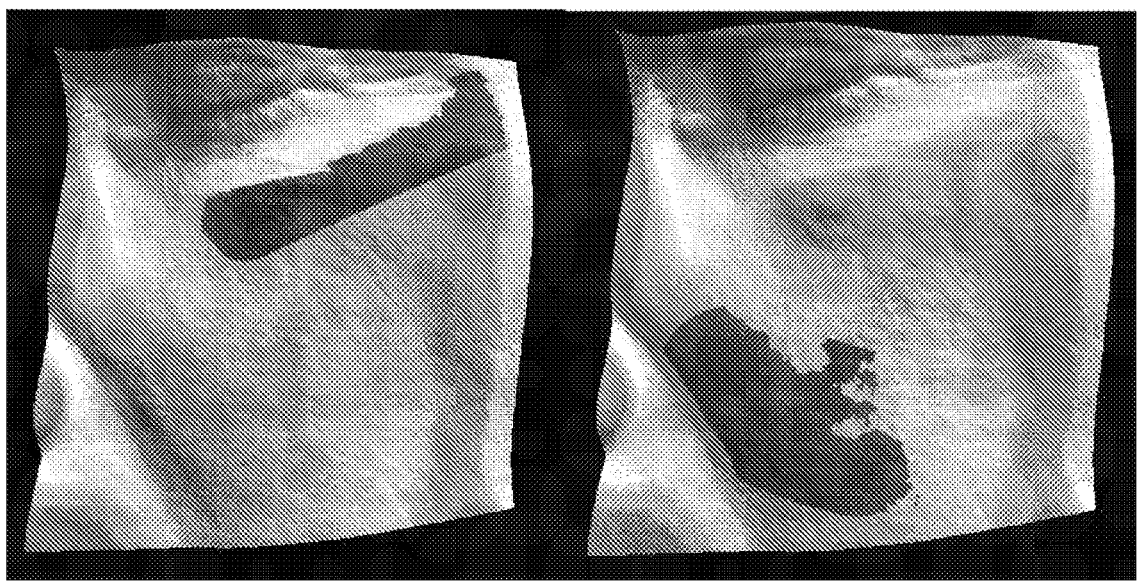
Figures 7I, 7J:
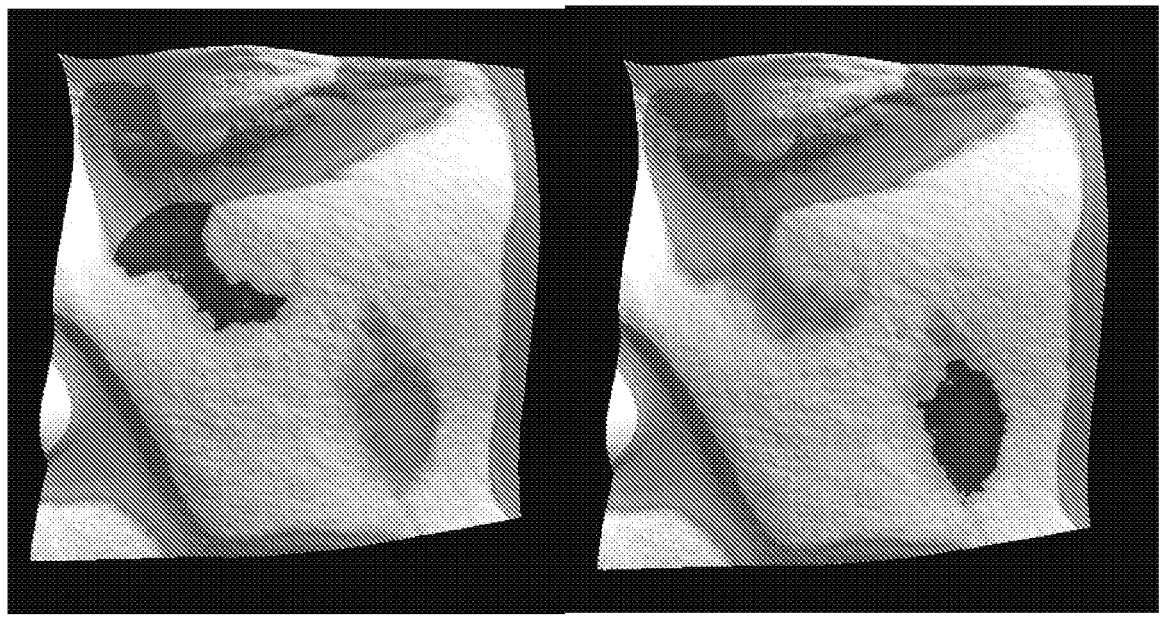
Figure 7K:
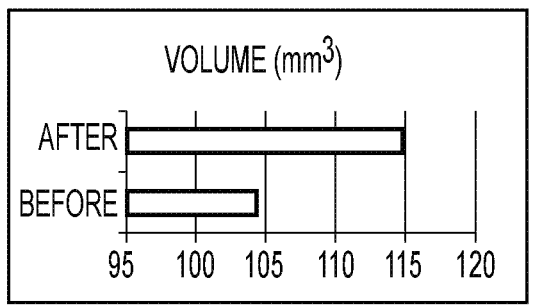
Figure 7L:
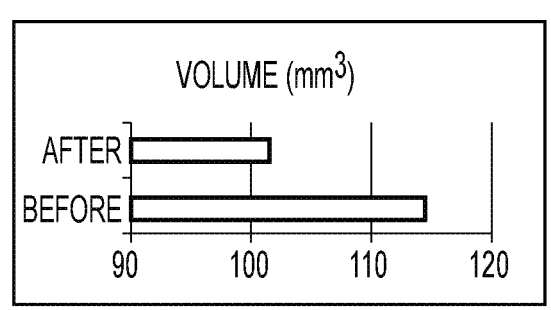
Figure 7M:
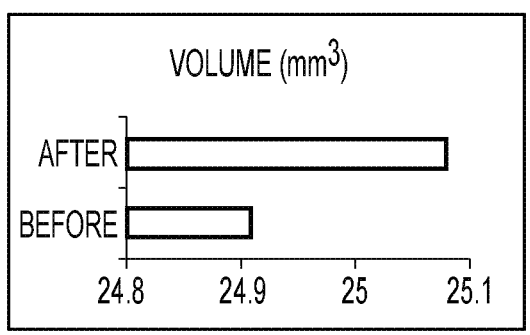
Figure 7N:
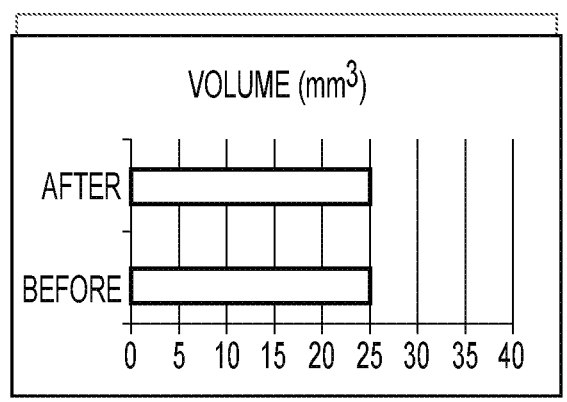

FIGS. 7A-7E and 7F-J show before and after photo images, respectively, of an individual being treated using the topical composition according to the invention. The topical composition according to the invention was applied to the left side of the face. The treatment period lasted 199 days with application no less frequent than once per day. FIGS. 7A and 7F show the before and after photo images. FIGS. 7B and 7G show before and after images topographically with areas of elevation appearing darker and with a highlighted portion of the cheekbone selected for quantification. FIG. 7K shows a graph comparing the volume in the highlighted sections of the cheekbone area in FIGS. 7B and 7G in cubic millimeters as computed automatically by the Antera system. The treatment resulted in a 10% increase in volume of the highlighted cheekbone area and represents a significant improvement in the elevation and definition of the cheekbone. FIGS. 7C and 7H show before and after images topographically with areas of elevation appearing darker and with a highlighted portion of the lower cheek selected for quantification. FIG. 7L shows a graph comparing the volume in the highlighted sections of the lower cheek in FIGS. 7C and 7H in cubic millimeters as computed automatically by the Antera system. The treatment resulted in an 11% decrease in volume in the highlighted area and represents a significant improvement in the appearance of sagging of the lower cheek. FIGS. 7D and 7I show before and after images topographically with areas of depression appearing darker and with a highlighted portion of the tear trough selected for quantification. FIG. 7M shows a graph comparing the volume in the highlighted sections of the tear trough in FIGS. 7D and 7I in cubic millimeters as computed automatically by the Antera system. The treatment resulted in a 30% increase in the volume in the highlighted area and represents a significant improvement in the appearance of insufficient volume or hollowing of the periorbital region. FIGS. 7E and 7J show before and after images of area topographically with areas of depression appearing darker and with a highlighted portion of the mid-cheek dimple selected for quantification. FIG. 7N shows a graph comparing the volume in the highlighted sections of the mid-cheek dimple in cubic millimeters as computed automatically by the Antera system. The treatment resulted in a no change in the volume in the highlighted area and demonstrates that no filling occurred in an area that did not require it.

Example 8

Figures 8A, 8B:
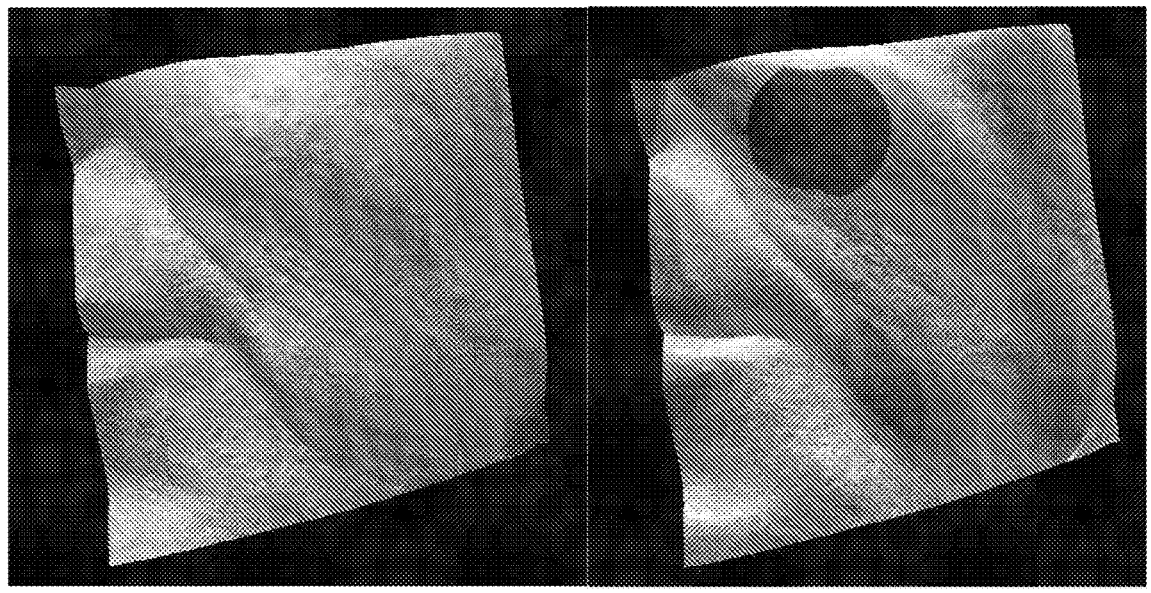
FIG. 8 shows before (in FIG. 8A, FIG. 8B, and FIG. 8C) and after (in FIG. 8D, FIG. 8E, and FIG. 8F) photo images taken using an Antera digital camera of an individual being treated using the topical composition according to an embodiment of the invention. The quantification of differences between the before and after images is shown in FIG. 8G (FIG. 8B vs.
FIG. 8D) and FIG. 8H (FIG. 8C vs.
FIG. 8E).
Figures 8C, 8D:
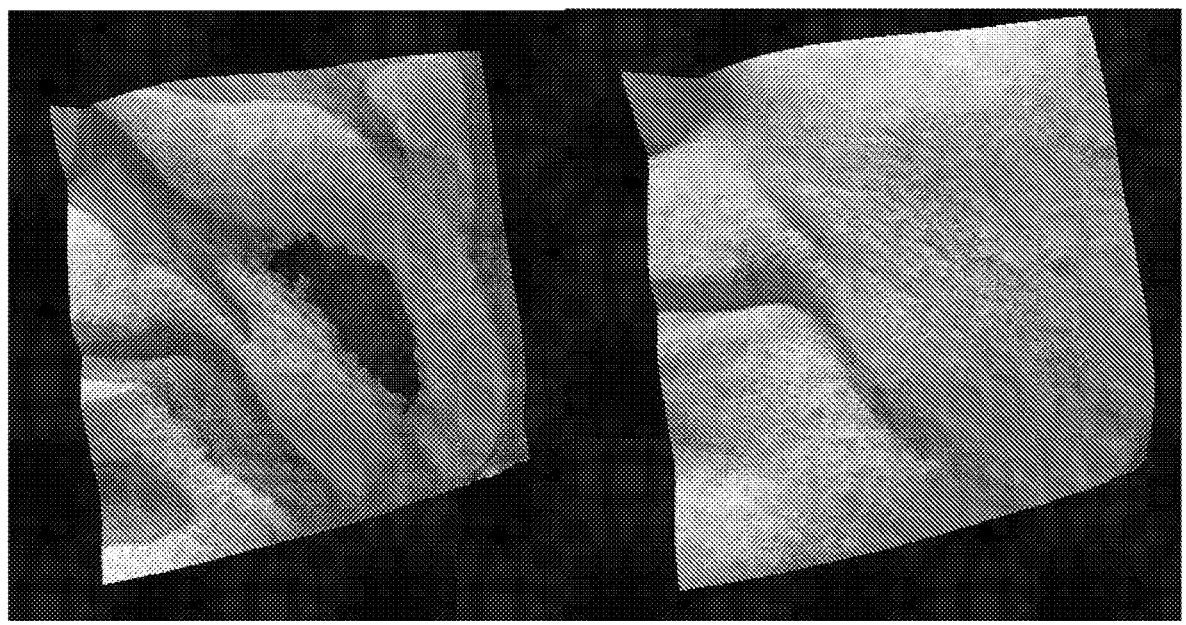

FIGS. 8A-8C and 8D-8F show before and after photo images, respectively, of an individual being treated using the topical composition according to the invention. The topical composition according to the invention was applied to the left side of the face. The treatment period lasted 105 days with application no less frequent than once per day. FIGS. 8A and 8F show the before and after photo images. FIGS. 8B and 8E show before and after images topographically with areas of elevation appearing darker and with a highlighted portion of the lower cheek area selected for quantification. FIG. 8G shows a graph comparing the volume in the highlighted sections of the lower cheek area in FIGS. 8B and 8E in cubic millimeters as computed automatically by the Antera system. The treatment resulted in a 18% decrease in volume in the lower cheek and represents a significant improvement in the appearance of sagging. FIGS. 8C and 8F show before and after images topographically with areas of depression appearing darker and with a highlighted portion of the mid-cheek dimple area selected for quantification. FIG. 8H shows a graph comparing the volume in the highlighted sections of the mid-cheek dimple in FIGS. 8C and 8F in cubic millimeters as computed automatically by the Antera system. The treatment resulted in a 14% decrease in volume in the highlighted area and represents a significant improvement in the appearance of jawline definition.

Example 9

FIGS. 9A-9C and 9D-8F show before and after photo images, respectively, of an individual being treated using the topical composition according to the invention. The topical composition according to the invention was applied to the left side of the face. The treatment period lasted 125 days with application no less frequent than once per day. FIGS. 9A and 9F show the before and after photo images. FIGS. 9B and 9E show before and after images topographically with areas of elevation appearing darker and with a highlighted portion of the upper cheek area selected for quantification. FIG. 9G shows a graph comparing the volume in the highlighted sections of the upper cheek area in FIGS. 9B and 9E in cubic millimeters as computed automatically by the Antera system. The treatment resulted in an 18% increase in volume in the selected portion of the upper cheek and represents a significant improvement in the appearance of sagging and definition of the upper cheek. FIGS. 9C and 9F show before and after images topographically with areas of depression appearing darker and with a highlighted portion of the mid-cheek dimple area selected for quantification. FIG. 9H shows a graph comparing the volume in the highlighted sections of the mid-cheek dimple in FIGS. 9C and 9F in cubic millimeters as computed automatically by the Antera system. The treatment resulted in a 64% decrease in volume in the highlighted area and represents a significant improvement in the appearance of jawline definition.

Example 10

Figure 10I:
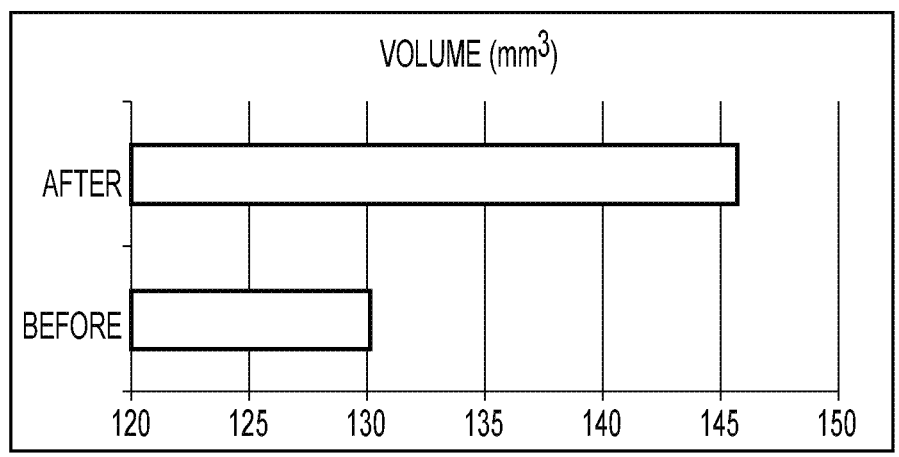
FIG. 10 shows before (in FIG. 10A, FIG. 10B, FIG. 10C, and FIG. 10D) and after (in FIG. 10E, FIG. 10F, FIG. 10G and FIG. 10H) photo images taken using an Antera digital camera of an individual being treated using the topical composition according to an embodiment of the invention. The quantification of differences between the before and after images is shown in FIG. 10I (FIG. 10B vs.
FIG. 10F), FIG. 10J (FIG. 10C vs.
FIG. 10G) and FIG. 10K (FIG. 10D vs. 10H).
Figure 10J:
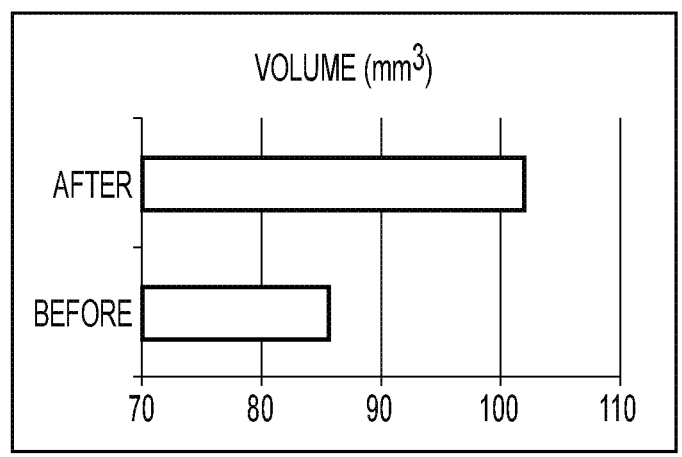
Figure 10K:
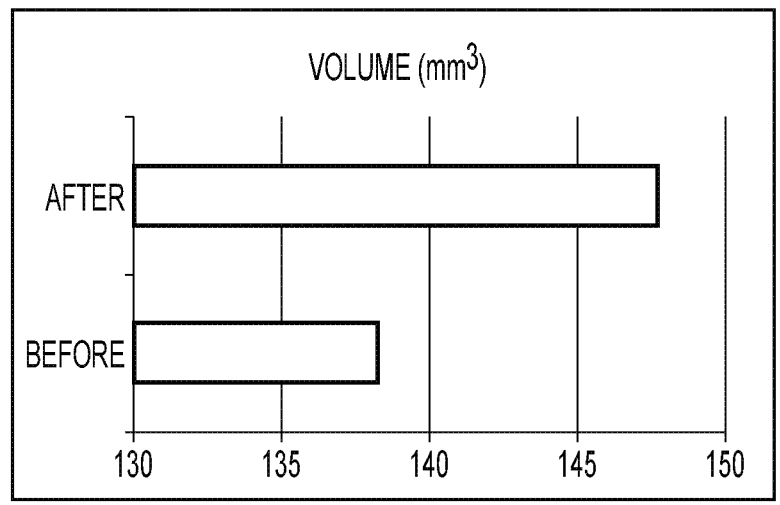

FIGS. 10A-D and 10E-10H show before and after photo images, respectively, of an individual being treated using the topical composition according to the invention. The topical composition according to the invention was applied to the right side of the face. The treatment period lasted 256 days with application no less frequent than once per day. FIGS. 10A and 10E show the before and after photo images. FIGS. 10B and 10F show before and after images topographically with areas of elevation appearing darker and with a highlighted portion of the cheekbone area selected for quantification. FIG. 10I shows a graph comparing the volume in the highlighted sections of the cheekbone area in FIGS. 10B and 10F in cubic millimeters as computed automatically by the Antera system. The treatment resulted in a 12% increase in volume in the selected cheekbone and represents a significant improvement in the elevation and definition of the cheekbone area. FIGS. 10C and 10G show before and after images topographically with areas of elevation appearing darker and with a highlighted portion of the upper cheek area selected for quantification. FIG. 10J shows a graph comparing the volume in the highlighted section of the upper cheek area in FIGS. 10C and 10G in cubic millimeters as computed automatically by the Antera system. The treatment resulted in a 19% increase in volume in the highlighted upper cheek area and represents a significant improvement in the appearance of upper cheek lifting and a reduction in the appearance of sagging. FIGS. 10D and 10H show before and after images topographically with areas of depression appearing darker and with a highlighted portion of the mid-cheek dimple area selected for quantification. FIG. 10K shows a graph comparing the volume in the highlighted section of the mid-cheek dimple area in FIGS. 10D and 10H in cubic millimeters as computed automatically by the Antera system. The treatment resulted in a 7% increase in mid-cheek indentation in the selected area and represents a significant improvement in the appearance of definition in the jawline.

Example 11

Figure 11A:
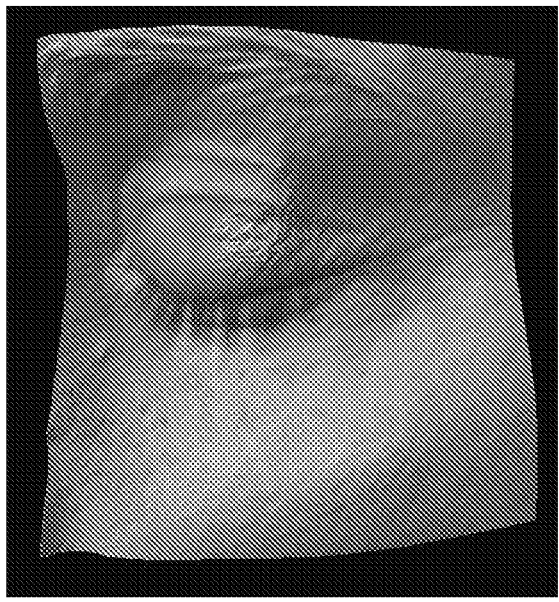
FIG. 11 shows before (in FIG. 11A, FIG. 11B, and FIG. 11C) and after (in FIG. 11D, FIG. 11E, and FIG. 11F) photo images taken using an Antera digital camera of an individual being treated using the topical composition according to an embodiment of the invention. The quantification of differences between the before and after images is shown in FIG. 11G (FIG. 11B vs.
FIG. 11D) and FIG. 11H (FIG. 11C vs.
FIG. 11E).
Figure 11B:
Figure 11C:
Figure 11D:
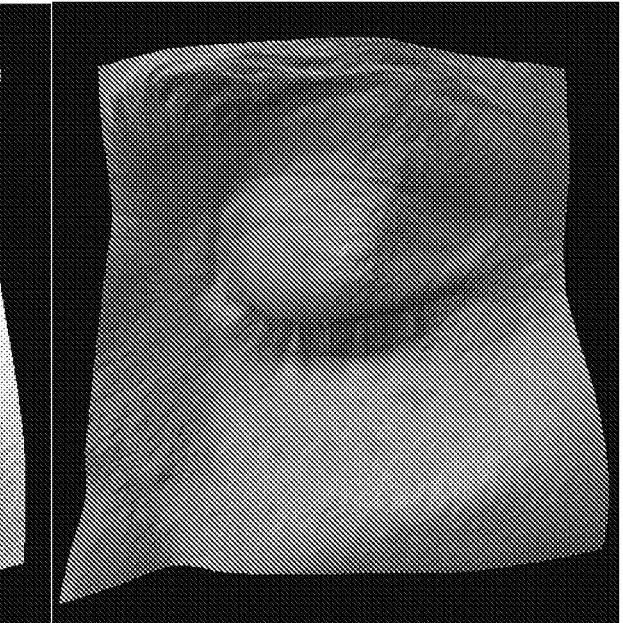

FIGS. 11A-11C and 11D-11F show before and after photo images, respectively, of an individual being treated using the topical composition according to the invention. The topical composition according to the invention was applied to the left side of the face, under the eye. The treatment period lasted 127 days with application no less frequent than once every other day. FIGS. 11A and 11D show the before and after photo images. FIGS. 11B and 11E show before and after images topographically with areas of depression appearing darker and with a highlighted portion of the tear trough area selected for quantification. FIG. 11G shows a graph comparing the volume in the highlighted sections of the tear trough area in FIGS. 11B and 11E in cubic millimeters as computed automatically by the Antera system. The treatment resulted in an 11% increase in volume in the selected tear trough area and represents a significant improvement reduction in hollowing in the periorbital area. FIGS. 11C and 11F show before and after images topographically with areas of elevation appearing darker and with a highlighted portion of the cheekbone area selected for quantification. FIG. 11H shows a graph comparing the volume in the highlighted section of the cheekbone area in FIGS. 11C and 11H in cubic millimeters as computed automatically by the Antera system. The treatment resulted in a 41% increase in volume in the selected cheekbone area and represents a significant improvement in the appearance of cheekbone area.

What is claimed is:

1. A topical composition effective for increasing superficial dermal fat volume or for decreasing superficial dermal fat volume as needed in a human, comprising: at least one adipogenic agent; at least one lipolytic agent; and at least one penetrant, wherein the at least one lipolytic agent is selected from the group consisting of: *Kaempferia parviflora* extract, *Cyclopia intermedia*, and *Phaseolus vulgaris* extract, and the at least one adipogenic agent is selected from the group consisting of: sunflower seed oil, chia oil, hemp oil, safflower oil, and mixtures thereof.

2. The topical composition of claim 1, wherein the at least one penetrant is selected from the group consisting of palmitate, isopropyl palmitate, isopropyl myristate, propylene glycol, and nonionic detergents.

* * * * *